(12) United States Patent
Jin et al.

(10) Patent No.: US 7,179,827 B2
(45) Date of Patent: Feb. 20, 2007

(54) THIAZOLES AND METHODS OF THEIR USE

(75) Inventors: Haihong Jin, Manalapan, NJ (US); Zhi-Cai Shi, Monmouth Junction, NJ (US); Heidi Theis, New York, NY (US); Hartmuth Kolb, Marina del Rey, CA (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 11/094,237

(22) Filed: Mar. 31, 2005

(65) Prior Publication Data

US 2005/0282807 A1    Dec. 22, 2005

Related U.S. Application Data

(60) Provisional application No. 60/557,702, filed on Mar. 31, 2004.

(51) Int. Cl.
| | | |
|---|---|---|
| *A61K 31/426* | (2006.01) | |
| *A61K 31/427* | (2006.01) | |
| *C07D 277/56* | (2006.01) | |
| *C07D 417/06* | (2006.01) | |

(52) U.S. Cl. ...................................... 514/370; 548/194
(58) Field of Classification Search ................ 548/194; 514/370
See application file for complete search history.

(56) References Cited

U.S. PATENT DOCUMENTS

| 5,247,076 A | 9/1993 | Goulet et al. |
|---|---|---|
| 5,317,101 A | 5/1994 | Oldfield et al. |
| 5,561,134 A | 10/1996 | Spada et al. |
| 5,652,366 A | 7/1997 | Spada et al. |
| 5,834,468 A | 11/1998 | Breault et al. |
| 5,874,432 A | 2/1999 | Dunlap et al. |
| 6,248,769 B1 | 6/2001 | Cavalla et al. |
| 6,489,476 B1 | 12/2002 | Dang et al. |
| 6,596,744 B2 | 7/2003 | Wagle et al. |
| 2002/0019527 A1 | 2/2002 | Wang et al. |
| 2002/0022622 A1 | 2/2002 | Wagle et al. |
| 2002/0032187 A1 | 3/2002 | Drake et al. |
| 2003/0018046 A1 | 1/2003 | Bridger et al. |
| 2003/0119970 A1 | 6/2003 | Husemann et al. |

FOREIGN PATENT DOCUMENTS

| WO | WO 93/13077 A1 | 7/1993 |
|---|---|---|
| WO | WO 97/24119 A1 | 7/1997 |
| WO | WO 98/17628 A1 | 4/1998 |
| WO | WO 98/28282 A2 | 7/1998 |
| WO | WO 98/46599 A1 | 10/1998 |
| WO | WO 99/21845 A2 | 5/1999 |
| WO | WO 99/47529 A1 | 9/1999 |
| WO | WO 01/56567 A1 | 8/2001 |
| WO | WO 01/81316 A2 | 11/2001 |
| WO | WO 02/053158 A1 | 7/2002 |
| WO | WO 02/083111 A2 | 10/2002 |
| WO | WO 03/004467 A2 | 1/2003 |
| WO | WO 03/062392 A2 | 7/2003 |
| WO | WO 03/078398 A1 | 9/2003 |

OTHER PUBLICATIONS

Golub et al., Science, vol. 286, Oct. 15, 1999, pp. 531-537.*

* cited by examiner

*Primary Examiner*—Laura L. Stockton
(74) *Attorney, Agent, or Firm*—Max Bachrach

(57) ABSTRACT

This invention concerns novel thiazole compounds. Methods of using these compounds for the treatment, prevention and management of various diseases or disorders, as well as pharmaceutical compositions of these compounds, are also disclosed.

16 Claims, No Drawings

THIAZOLES AND METHODS OF THEIR USE

This application claims priority to U.S. Provisional Application No. 60/557,702, filed Mar. 31, 2004, which is incorporated herein in its entirety by reference.

1. FIELD OF THE INVENTION

This invention relates to novel thiazoles and methods of their use for the treatment, prevention and management of various diseases and disorders, such as neurological and psychiatric disorders/diseases, cancer, and disorders mediated by protein kinase inhibition.

2. BACKGROUND OF THE INVENTION

Protein Kinases (PKs) are enzymes that catalyze the phosphorylation of hydroxyl groups on tyrosine, serine and threonine residues of proteins. The phosphorylation of proteins modulates various cell activities such as cell growth, differentiation and proliferation. Abnormal PK activity has been related to a host of disorders, ranging from conditions such as psorisasis to life-threatening diseases such as glioblastoma (brain cancer).

A great deal of effort has been expended in attempts to identify ways of modulating PK activity. Examples include: biomimetic approaches using large molecules patterned on those involved in the actual cellular processes (e.g., mutant ligands (U.S. Pat. No. 4,966,849); soluble receptors and antibodies (WO 94/10202, Kendall et al., *Proc. Nat'l Acad. Sci.*, 90: 10705–09 (1994), Kim et al., *Nature*, 362: 841–844 (1993)); RNA ligands (Jelinek et al., *Biochemistry*, 33: 10450–56); Takano et al., *Mol. Bio. Cell*, 4: 358A (1993); Kinsella et al., *Exo. Cell Res.*, 199: 56–62 (1992); Wright et al., *J. Cellular Phys.*, 152: 448–57); and tyrosine kinase inhibitors (WO 94/03427; WO 92/21660; WO 91/15495; WO 94/14808; U.S. Pat. No. 5,330,992; Mariani et al., *Proc. Am. Assoc. Cancer Res.*, 35: 2268 (1994)). Despite such attempts, a need still exists for effective methods of modulating PK activity.

3. SUMMARY OF THE INVENTION

This invention encompasses compounds of formula (1):

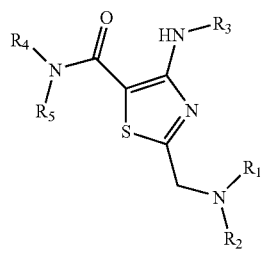

(1)

wherein:

$R_1$, $R_2$, $R_3$, $R_4$ and $R_5$ are each independently H, optionally substituted alkyl, optionally substituted alkenyl, optionally substituted alkynyl, optionally substituted aryl, optionally substituted heteroaryl, optionally substituted heterocycloalkyl, optionally substituted heterocycle; optionally substituted arylalkyl, optionally substituted heterocycloalkylalkyl, optionally substituted heteroarylalkyl, optionally substituted alkoxycarbonyl, optionally substituted aminocarbonyl, optionally substituted carbonyl, or optionally substituted sulfonyl; or $R_1$ and $R_2$, and $R_4$ and $R_5$, with the nitrogen atom to which they are attached, independently form an optionally substituted heterocycle;

and pharmaceutically acceptable salts, solvates, stereoisomers and prodrugs thereof.

In one specific embodiment, $R_3$ is alkyl.

In another specific embodiment, $R_1$ and $R_2$, with the nitrogen atom to which they are attached form an optionally substituted heterocycle.

In another specific embodiment, the heterocycle formed by $R_1$ and $R_2$ is optionally substituted piperidine.

In another specific embodiment, the heterocycle formed by $R_1$ and $R_2$ is optionally substituted morpholine.

In yet another specific embodiment, the heterocycle formed by $R_1$ and $R_2$ is optionally substituted piperazine.

In yet another specific embodiment, $R_4$ is H and $R_5$ is alkyl or cycloalkyl.

In yet another specific embodiment, $R_4$ is H and $R_5$ is optionally substituted aminocarbonyl.

In yet another specific embodiment, the heterocycle formed by $R_4$ and $R_5$ is optionally substituted pyrrolidine.

Another embodiment of this invention encompasses pharmaceutical compositions comprising compounds of formula (1), or pharmaceutically acceptable salts, solvates, stereoisomers or prodrugs thereof.

In another embodiment, this invention encompasses methods of treating, preventing and managing various diseases and disorders, which comprise administering to a patient in need of such treatment, prevention or management a therapeutically or prophylactically effective amount of a compound of formula (1), or a pharmaceutically acceptable salt, solvate, stereoisomer or prodrug thereof.

4. DETAILED DESCRIPTION OF THE INVENTION

This invention encompasses novel thiazole compounds and their pharmaceutical compositions. Compounds of the invention are useful in treating, preventing and managing various diseases or disorders. Examples of diseases or disorders include, but are not limited to: allergic disorders (e.g., immunodeficiency diseases and hypersensitivity); cardiovascular disorders (e.g., hypertension and arteriosclerosis); dental and oral disorders (e.g., inflammation of the oral mucosa); dermatologic disorders (e.g., dermatitis and skin infections); disorders due to physical agents (e.g., altitude or motion sickness); endocrine and metabolic disorders (e.g., hypopituitarism and hyperthyroism); gastrointestinal disorders (e.g., inflammatory bowel disease and pancreatitis); gentourinary disorders (e.g., urinary incontinence and myoneurogenic disorders); gynecologic and obstetrics disorders (e.g., sexual dysfunction and gynecologic inflammations); hematological and oncologic disorders (e.g., anemias, myeloproliferative disorder and cancer); hepatic and biliary disorders (e.g., fatty liver and hepatitis); infectious diseases (e.g., diseases caused by bacterial, viral or fungal infections); musculoskeletal and connective tissue disorders (e.g., rheumatoid arthritis and systemic sclerosis); neurologic disorders (e.g., pain and sleep disorders); nutritional disorders (e.g., protein-energy malnutrition); ophthalmologic disorders (e.g., conjunctivitis and keratitis); psychiatric disorders (e.g., anxiety and mood disorders); and pulmonary disorders (e.g., asthma and bronchitis).

4.1 Definitions

Unless otherwise specified, the meanings of various terms and phrases used herein are described below.

The term "alkyl" means a saturated straight chain or branched hydrocarbon having from 1 to 20 carbon atoms, specifically, 1–10 carbon atoms, more specifically, 1–4 carbon atoms. An alkyl group is an optionally substituted straight, branched or cyclic (cycloalkyl) saturated hydrocarbon group. When substituted, alkyl groups may be substituted as described herein at any available point of attachment. An alkyl group substituted with an alkyl group may be referred to as a "branched alkyl group." Examples of unsubstituted alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl. Alkyl groups may also comprise one or more carbon-to-carbon double bonds or one or more carbon-to-carbon triple bonds.

The term "alkenyl" means a straight chain or branched hydrocarbon having from 2 to 20 carbon atoms, specifically, 2–10 carbon atoms, more specifically, 2–6 carbon atoms, and including at least one carbon-carbon double bond. Representative straight chain and branched ($C_2$–$C_{10}$)alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, and 3-decenyl. The double bond of an alkenyl group may be unconjugated or conjugated to another unsaturated group. An alkenyl group may be unsubstituted or substituted.

The term "alkynyl" means a straight chain or branched non-cyclic hydrocarbon having from 2 to 20 carbon atoms, specifically, 2–10 carbon atoms, more specifically, 2–6 carbon atoms, and including at lease one carbon-carbon triple bond. Representative straight chain and branched ($C_2$–$C_{10}$) alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. The triple bond of an alkynyl group may be unconjugated or conjugated to another unsaturated group. An alkynyl group may be unsubstituted or substituted.

The term "alkoxy" means an alkyl group bonded through an oxygen linkage (—O—). Examples of alkoxy include, but are not limited to, —$OCH_3$, —$OCH_2CH_3$, —$O(CH_2)_2CH_3$, —$O(CH_2)_3CH_3$, —$O(CH_2)_4CH_3$, and —$O(CH_2)_5CH_3$.

The term "aryl" refers to monocyclic and bicyclic aromatic rings, e.g., phenyl, as well as groups that are fused, e.g., napthyl or phenanthrenyl. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more substituents as defined herein. Representative aryl groups include, but are not limited to, phenyl, tolyl, anthracenyl, fluorenyl, indenyl, azulenyl, phenanthrenyl and naphthyl.

The term "arylalkyl" refers to an aromatic ring bonded to an alkyl group.

The term "cycloalkyl" means a specie of alkyl containing from 3 to 15 carbon atoms, without alternating or resonating double bonds between carbon atoms. It may contain from 1 to 4 rings. Examples of unsubstituted cycloalkyls include, but are not limited to, cyclopropyl, cyclobutyl, cyclopentyl, cyclohexyl, and adamantyl. A cycloalkyl may be substituted with one or more of the substituents as defined below.

The term "halogen" or "halo" refers to chlorine, bromine, fluorine or iodine.

The term "heteroalkyl" refers to an alkyl moiety, which comprises a heteroatom such as N, O, P, B, S, Si, Sb, Al, Sn, As, Se, or Ge. The heteroatom connected to the rest of the heteroalkyl moiety by a saturated or unsaturated bond. Thus, an alkyl substituted with a group, such as heterocycloalkyl, substituted heterocycloalkyl, heteroaryl, substituted heteroaryl, alkoxy, aryloxy, boryl, phosphino, amino, silyl, thio, or seleno, is within the scope of the term heteroalkyl. Examples of heteroalkyls include, but are not limited to, cyano, benzoyl, 2-pyridyl and 2-furyl.

The term "heteroaryl" means a carbocyclic aromatic ring containing from 5 to 14 ring atoms, of which at least one (e.g., one, two, or three) is a heteroatom (e.g., nitrogen, oxygen, or sulfur). Heteroaryl ring structures include, but are not limited to, mono-, bi-, and tricyclic compounds, as well as fused heterocyclic moieties. Examples of heteroaryls include, but are not limited to, triazolyl, tetrazolyl, oxadiazolyl, pyridyl, furyl, benzofuranyl, thiophenyl, thiazolyl, benzothiophenyl, benzoisoxazolyl, benzoisothiazolyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, acridinyl, pyrimidyl, oxazolyl, benzo[1,3]dioxole and 2,3-dihydro-benzo[1,4]dioxine. A group maybe unsubstituted or substituted.

The term "heteroarylalkyl" means a heteroaryl group to which an alkyl group is attached.

The term "heterocycle" means a monocyclic or polycyclic ring comprising carbon and hydrogen atoms, optionally having 1 or 2 multiple bonds, and the ring atoms contain at least one heteroatom, specifically 1 to 3 heteroatoms, independently selected from nitrogen, oxygen, and sulfur. Heterocycle ring structures include, but are not limited to, mono-, bi-, and tri-cyclic compounds. Specific heterocycles are monocyclic or bicyclic. Representative heterocycles include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl and tetrahydrothiopyranyl. A heterocyclic ring may be unsubstituted or substituted.

The term "heterocycloalkyl" refers to a cycloalkyl group in which at least one of the carbon atoms in the ring is replaced by a heteroatom (e.g., O, S or N).

The term "heterocycloalkylalkyl" means a heterocycloalkyl group to which an alkyl group is attached.

The term "substituted," when used to describe a chemical structure or moiety, refers to a derivative of that structure or moiety wherein one or more of its hydrogen atoms is replaced with a substituent such as, but not limited to, alkyl, alkenyl, alkynyl, cycloalkyl, aroyl, halo, haloalkyl (e.g., trifluoromethyl), heterocycloalkyl, haloalkoxy (e.g., trifluoromethoxy), hydroxy, alkoxy, cycloalkyloxy, heterocylooxy, oxo, alkanoyl, aryl, substituted aryl, heteroaryl (e.g., indolyl, imidazolyl, furyl, thienyl, thiazolyl, pyrrolidyl, pyridyl, and pyrimidyl), arylalkyl, alkylaryl, heteroaryl, heteroarylalkyl, alkylheteroaryl, heterocyclo, aryloxy, alkanoyloxy, amino, alkylamino, arylamino, arylalkylamino, cycloalkylamino, heterocycloamino, mono- and di-substituted amino, alkanoylamino, aroylamino, aralkanoylamino, substituted alkanoylamino, substituted arylamino, substituted aralkanoylamino, carbamyl (e.g., $CONH_2$), substituted carbamyl (e.g., CONH-alkyl, CONH-aryl, CONH-arylalkyl or instances where there are two substituents on the nitrogen), carbonyl, alkoxycarbonyl, carboxy, cyano, ester, ether, guanidino, nitro, sulfonyl, alkylsulfonyl, arylsulfonyl, arylalkylsulfonyl, sulfonamido (e.g., $SO_2NH_2$), substituted sulfonamido, thiol, alkylthio, arylthio, arylalkylthio, cycloalkylthio, heterocyclothio, alkylthiono, arylthiono and arylalkylthiono. In some embodiments, a substituent itself may be substituted with one or more chemical moieties such as, but not limited to, those described herein.

The term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc and organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

The term "solvate" means a compound or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein, and unless otherwise indicated, the terms "biohydrolyzable amide," "biohydrolyzable ester," "biohydrolyzable carbamate," "biohydrolyzable carbonate," "biohydrolyzable ureido," "biohydrolyzable phosphate" mean an amide, ester, carbamate, carbonate, ureido, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein, and unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

The terms "treat," "treating" and "treatment," as used herein, contemplate an action that occurs while a patient is suffering from the specified disease or disorder, which reduces the severity of the disease or disorder, or retards or slows the progression of the disease or disorder.

As used herein, unless otherwise indicated, the terms "prevent," "preventing" and "prevention" contemplate an action that occurs before a patient begins to suffer from the specified disease or disorder, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, and unless otherwise specified, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

As used herein, and unless otherwise specified, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

It should be noted that if there is a discrepancy between a depicted structure and a name given that structure, the structure should be accorded more weight. In addition, if the stereochemistry of a structure or a portion of a structure is not indicated with, for example, bold or dashed lines, the structure or the portion of the structure is to be interpreted as encompassing all stereoisomers of it.

4.2 Compounds of the Invention

This invention encompasses compounds of formula (1):

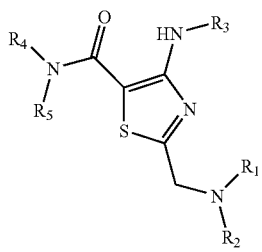

(1)

wherein:
$R_1$, $R_2$, $R_3$, $R_4$ and $R_5$ are each independently H, optionally substituted alkyl, optionally substituted alkenyl, optionally substituted alkynyl, optionally substituted aryl, optionally substituted heteroaryl, optionally substituted heterocycloalkyl, optionally substituted heterocycle; optionally substituted arylalkyl, optionally substituted heterocycloalkylalkyl, optionally substituted heteroarylalkyl, optionally substituted alkoxycarbonyl, optionally substituted aminocarbonyl, optionally substituted carbonyl, or optionally substituted sulfonyl; or
$R_1$ and $R_2$, and $R_4$ and $R_5$, with the nitrogen atom to which they are attached, independently form an optionally substituted heterocycle;
and pharmaceutically acceptable salts, solvates, stereoisomers and prodrugs thereof.

In one specific embodiment, $R_3$ is alkyl.

In another specific embodiment, $R_1$ and $R_2$, with the nitrogen atom to which they are attached, form an optionally substituted heterocycle.

In another specific embodiment, $R_1$ and $R_2$, with the nitrogen atom to which they are attached, form an optionally substituted heterocycle, and $R_4$ and $R_5$ do not form a heterocycle.

In another specific embodiment, the heterocycle formed by $R_1$ and $R_2$ is optionally substituted piperidine.

In another specific embodiment, the heterocycle formed by $R_1$ and $R_2$ is optionally substituted morpholine.

In yet another specific embodiment, the heterocycle formed by $R_1$ and $R_2$ is optionally substituted piperazine.

In yet another specific embodiment, $R_4$ is H and $R_5$ is alkyl or cycloalkyl.

In yet another specific embodiment, $R_4$ is H and $R_5$ is optionally substituted aminocarbonyl.

In another specific embodiment, $R_4$ and $R_5$, with the nitrogen atom to which they are attached, form an optionally substituted heterocycle.

In another specific embodiment, $R_4$ and $R_5$, with the nitrogen atom to which they are attached, form an optionally substituted heterocycle, and $R_1$ and $R_2$ do not form a heterocycle.

In yet another specific embodiment, the heterocycle formed by $R_4$ and $R_5$ is optionally substituted pyrrolidine.

Specific examples of compounds of this invention include those shown in Table 1, and pharmaceutically acceptable salts, solvates, stereoisomers, and prodrugs thereof:

TABLE 1

| Compound | Structure |
|---|---|
| 1 | 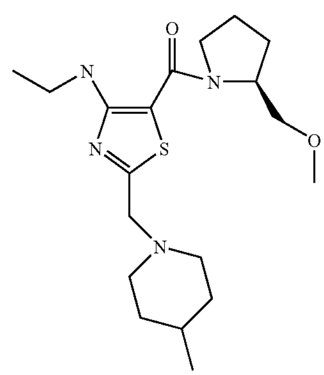 |
| 2 | 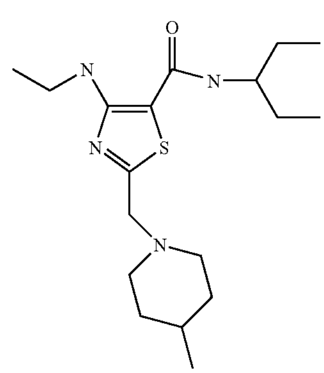 |

TABLE 1-continued

| Compound | Structure |
|---|---|
| 3 | (4-methylamino-2-(piperidin-1-ylmethyl)thiazole-5-carboxylic acid cyclopropylamide) |
| 4 | (4-methylamino-2-(piperidin-1-ylmethyl)thiazole-5-carboxylic acid cyclopentylamide) |
| 5 | (4-(2-methoxyethylamino)-2-(morpholin-4-ylmethyl)thiazole-5-carboxylic acid N-(2-(dimethylamino)-2-oxoethyl)amide) |
| 6 | (4-ethylamino-2-((4-(4-chlorophenyl)piperazin-1-yl)methyl)thiazole-5-carboxylic acid sec-butylamide) |
| 7 | (4-ethylamino-2-((4-(4-chlorophenyl)piperazin-1-yl)methyl)thiazole-5-carboxylic acid N-(1-methyl-2-methoxyethyl)amide) |
| 8 | (4-propylamino-2-((4-benzylpiperazin-1-yl)methyl)thiazole-5-carboxylic acid N-(1-methyl-2-methoxyethyl)amide) |
| 9 | (4-hexylamino-2-(piperidin-1-ylmethyl)thiazole-5-carboxylic acid cyclopropylamide) |
| 10 | (4-hexylamino-2-(piperidin-1-ylmethyl)thiazole-5-carboxylic acid N-(pentan-3-yl)amide) |

Various compounds of the invention may contain one or more stereocenters, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions*, p. 268 (E. L. Eliel, Ed., Univ. of Notre Dame Press, Notre Dame, Ind., 1972).

Compounds of this invention may be in amorphous or crystalline form. Crystalline compounds of the invention can exist in one or more polymorphs, all of which are encompassed by this invention.

4.3 Preparation of Compounds of the Invention

Various compounds of the invention can be prepared using the general synthesis methods described herein. Compounds of formula IX may be prepared by the synthetic route described in Scheme 1:

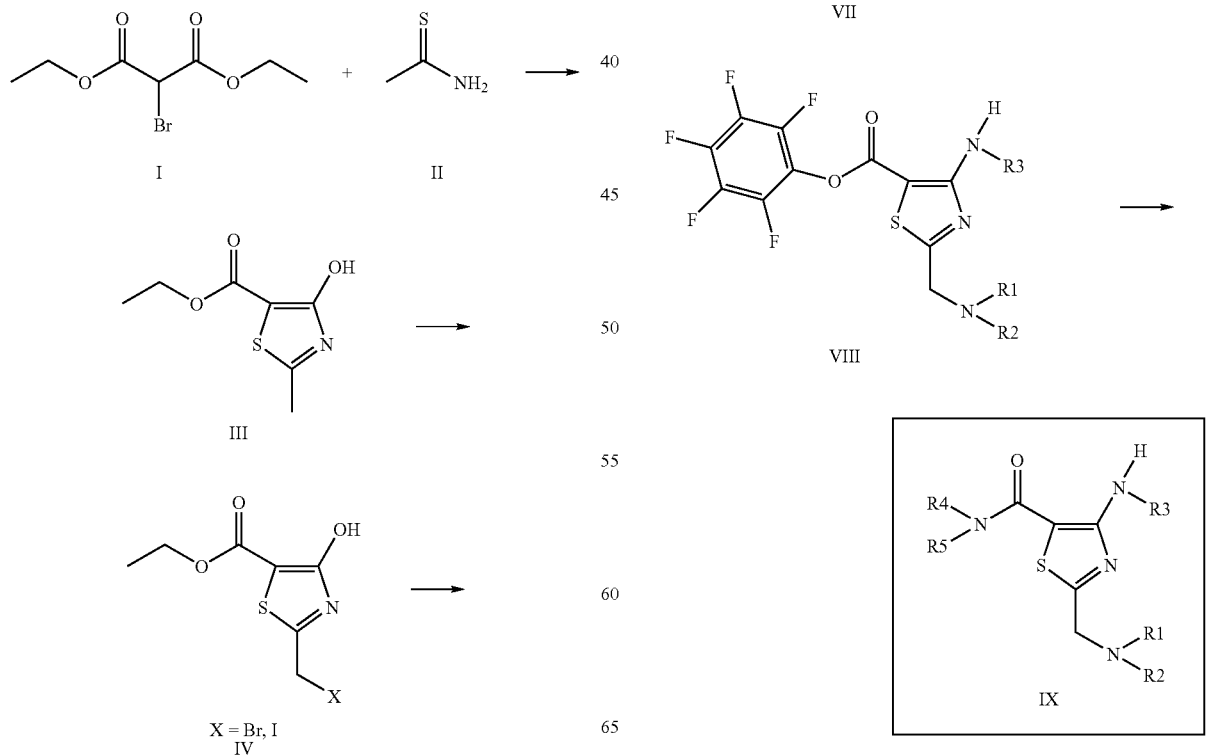

Compounds of formula III may be prepared by a reaction of compound I and compound II in an organic solvent at temperature of about 50 to about 250° C., preferably at about 10 to about 150° C., for about 0.5 to 24 hours. Suitable solvents include benzene, toluene, xylene, and N,N-dimethylformamide.

Compound III may be converted to a compound of formula IV by reacting with a halogenating reagent such as N-bromo-succinimide or N-iodo-succinimide in an organic solvent at temperature of about −20° C. to about 100° C., preferably at about 0° C. to room temperature, for about 1 to 24 hours. Suitable solvents include chloroform, carbon tetrachloride, tetrahydrofuran, and methylene chloride.

Compounds of formula V are then formed by a reaction of compound IV with para-tosyl chloride in the presence of an organic base and an organic solvent at a temperature of about −20° C. to about 100° C. for about 1 to 48 hours. Suitable bases include triethylamine, N,N-diisopropyl ethylamine, pyridine, and 2,6-lutidine. Suitable organic solvents include methylene chloride, dichloroethane, chloroform, tetrahydrofuran, and diethyl ether.

Compounds of formula VI may be prepared by a reaction of a compound of formula V and a secondary amine in an organic solvent at a temperature of about 0° C. to about 100° C., conveniently at room temperature, for about 1 hour to 2 days. Suitable organic solvents include tetrahydrofuran, chloroform, toluene, N,N-dimethylformamide, methylene chloride, and 1,4-dioxane.

Compounds of formula VII may be prepared by a reaction of a compound of formula VI with a primary amine in an organic solvent at a temperature of about 50° C. to about 250° C., preferably at about 100° C. to about 150° C., for about 5 to 48 hours. Suitable solvents include 1,4-dioxane, toluene, N,N-dimethylformamide, and 1-butanol.

Compounds of formula VII may be converted to a compound of formula VIII by first reacting with a base in a mixture of organic solvent and water at temperature of about 0° C. to about 100° C. for about 1 to 24 hours to give corresponding acid. Suitable bases include sodium hydroxide, potassium hydroxide, lithium hydroxide, and calcium hydroxide. Suitable organic solvents include ethanol, methanol, and tetrahydrofuran. Then, the acid is reacted with pentafluorophenol using a coupling reagent, such as O-(7-azabenzotriazol-1-yl)-N,N,N'N'-tetramethyluronium hexafluorophosphate, 0-benzotriazol-1-yl-N,N,N'N'-tetramethyluronium hexafluorophosphate and bromo-tris-pyrrolidino-phosphonium hexafluorophosphate, in an organic solvent at a temperature of about 0° C. to about 100° C. for 1 to 24 hours to give a compound of formula VIII. Suitable solvents include THF, methylene chloride, chloroform, and toluene.

Compounds of formula IX may be prepared by a reaction of a compound of formula VIII with an amine in an organic solvent and a base at temperature of about 25° C. to about 150° C. for 1 to 48 hours. Suitable bases include triethylamine, N,N-diisopropylethylamine and polymer supported diisopropylethylamine. Suitable solvents include tetrahydrofuran, methylene chloride, N,N-dimethylformamide, toluene, and 1,4-dioxane.

4.4 Pharmaceutical Compositions

This invention encompasses pharmaceutical compositions and dosage forms comprising compounds described herein. Pharmaceutical compositions and dosage forms of this invention may optionally contain one or more pharmaceutically acceptable carriers or excipients. Certain pharmaceutical compositions are single unit dosage forms suitable for oral, topical, mucosal (e.g., nasal, pulmonary, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. In another example, the compounds of this invention may be administered in a liposomal formulation to shield the compounds from degradative enzymes, facilitate transport in circulatory system, and effect delivery across cell membranes to intracellular sites.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

4.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants or lubricants can be used in pharmaceutical compositions and dosage forms of the invention.

The dosage forms of the invention may optionally comprise an enteric coating to provide release of the active ingredient in parts other than gastrointestinal region. The enteric coating material may be used in addition to, or instead of, other suitable coating materials. Examples of suitable enteric polymers include, but are not limited to, cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures thereof. Enteric coating may be provided using any suitable methods known in the art, including, but not limited to, spary-application of enteric polymers over a sub-coating.

4.4.2 Parenteral Dosage Forms

Parenteral dosage forms can be administered to patients by various routes including, but not limited to, subcutaneous, intravenous (including bolus injection), intramuscular, and intraarterial. Because their administration typically bypasses patients'natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; and water-miscible vehicles such as, but not limited to, ethyl alcohol, polyethylene glycol, and polypropylene glycol.

Compounds that increase the solubility of one or more of the active ingredients (i.e., the compounds of this invention) disclosed herein can also be incorporated into the parenteral dosage forms of the invention.

4.4.3 Transdermal, Topical and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, additional penetration enhancers can be used to assist in delivering the active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, prodrugs, clathrates, hydrates or solvates of the active ingredients can be used to further adjust the properties of the resulting composition.

4.4.4 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the compounds of this invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.5 Kits

In some cases, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a single unit dosage form of the compounds of this invention, or a pharmaceutically acceptable salt, prodrug, solvate, hydrate, clathrate or stereoisomer thereof, and a single unit dosage form of another agent that may be used in combination with the compounds of this invention. Kits of the invention can further comprise devices that are used to administer the active ingredients. Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. However, in specific embodiments, the formulations of the invention do not contain any alcohols or other co-solvents, oils or proteins.

The invention is further defined by reference to the following non-limiting examples. It will be apparent to those skilled in the art that many modifications, both to materials and methods, can be practiced without departing from the spirit and scope of this invention.

4.5 Methods of Treatment, Prevention, and Management

This invention encompasses methods of treating, preventing, and managing various diseases and disorders using the compounds described herein. Examples of diseases and disorders include, but are not limited to: allergic disorders (e.g., immunodeficiency diseases and hypersensitivity); cardiovascular disorders (e.g., hypertension and arteriosclerosis); dental and oral disorders (e.g., inflammation of the oral mucosa); dermatologic disorders (e.g., dermatitis and skin infections); disorders due to physical agents (e.g., altitude or motion sickness); endocrine and metabolic disorders (e.g., hypopituitarism and hyperthyroism); gastrointestinal disorders (e.g., inflammatory bowel disease and pancreatitis); gentourinary disorders (e.g., urinary incontinence and myoneurogenic disorders); gynecologic and obstetrics disorders (e.g., sexual dysfunction and gynecologic inflammations); hematological and oncologic disorders (e.g., anemias, myeloproliferative disorder and cancer); hepatic and biliary disorders (e.g., fatty liver and hepatitis); infectious diseases (e.g., diseases caused by bacterial, viral or fungal infections); musculoskeletal and connective tissue disorders (e.g., rheumatoid arthritis and systemic sclerosis); neurologic disorders (e.g., pain and sleep disorders); nutritional disorders (e.g., protein-energy malnutrition); ophthalmologic disorders (e.g., conjunctivitis and keratitis); psychiatric disorders (e.g., anxiety and mood disorders); and pulmonary disorders (e.g., asthma and bronchitis). All of these disorders are well-known in the art. See, *Merck Manual of Diagnosis and Therapy*, 17$^{th}$ Ed. (1999), which is incorporated herein by reference.

In a specific embodiment, this invention encompasses methods of treating, preventing, and managing cancer using compounds of the invention, or pharmaceutically acceptable salts, solvates, stereoisomers, or prodrugs thereof.

Cancers may be solid or blood-borne. Examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds of the invention can be used for treating, preventing or managing either primary or metastatic tumors.

Specific examples of cancer include, but are not limited to: AIDS associated leukemia and adult T-cell leukemia lymphoma; anal carcinoma; astrocytoma; biliary tract cancer; cancer of the bladder, including bladder carcinoma; brain cancer, including glioblastomas and medulloblastomas; breast cancer, including breast carcinoma; cervical cancer; choriocarcinoma; colon cancer including colorectal carcinoma; endometrial cancer; esophageal cancer; Ewing's sarcoma; gastric cancer; gestational trophoblastic carcinoma; glioma; hairy cell leukemia; head and neck carcinoma; hematological neoplasms, including acute and chronic lymphocytic and myelogeneous leukemia; hepatocellular carcinoma; Kaposi's sarcoma; kidney cancer; multiple myeloma; intraepithelial neoplasms, including Bowen's disease and Paget's disease; liver cancer; lung cancer including small cell carcinoma; lymphomas, including Hodgkin's disease, lymphocytic lymphomas, non-Hodgkin's lymphoma, Burkitt's lymphoma, diffuse large cell lymphoma, follicular mixed lymphoma, and lymphoblastic lymphoma; lymphocytic leukemia; neuroblastomas; oral cancer, including squamous cell carcinoma; ovarian cancer, including those arising from epithelial cells, stromal cells, germ cells and mesenchymal cells; pancreatic cancer; prostate cancer; rectal cancer; sarcomas, including soft tissue sarcomas, leiomyosarcoma, rhabdomyosarcoma, liposcarcoma, fibrosarcoma, and osteosarcoma; skin cancer, including melanoma, Kaposi's sarcoma, basal cell cancer and squamous cell cancer; testicular cancer, including testicular carcinoma and germinal tumors (e.g., semicoma, non-seminoma [teratomas, choriocarcinomas]), stromal tumors and germ cell tumors; thyroid cancer, including thyroid adenocarcinoma and medullar carcinoma; and renal cancer including adenocarcinoma and Wilm's tumor.

Other specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

Doses of compounds of the invention vary depending on factors such as: specific indication to be treated, prevented, or managed; age and condition of a patient; and amount of second active agent used, if any. Generally, the compounds may be used in an amount of from about 0.01 mg to about 2000 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 0.1 mg to about 1000 mg, from about 0.1 mg to about 500 mg, from about 0.1 mg to about 100 mg, from about 0.1 mg to about 50 mg, from about 0.1 mg to 10 mg, from about 1 mg to about 1000 mg, from about 1 mg to about 500 mg, from about 1 mg to about 100 mg, from about 1 mg to about 50 mg, from about 1 mg to about 10 mg, from about 10 mg to about 1000 mg, from about 10 mg to about 500 mg, from about 10 mg to 100 mg, from about 10 mg to 50 mg, from about 50 mg to about 500 mg, from about 50 mg to 200 mg, or from about 100 mg to 300 mg per day.

This invention also encompasses the use of compounds of the invention in combination with one or more second active agents. Second active agents can be large molecules (e.g., proteins) or small molecules (e.g., synthetic inorganic, organometallic, or organic molecules). Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40 ); histone deacetlyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Specific second active compounds that can be combined with compounds of this invention vary depending on the specific indication to be treated, prevented or managed.

Examples of second active agents that may be used for the treatment, prevention, and/or management of cancer include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfuilvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL- PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Other second active agents include, but are not limited to, 2-methoxyestradiol, telomestatin, inducers of apoptosis in mutiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil'), paclitaxel, ganciclovir, adriamycin, estramustine sodium phosphate (Emcyt®), sulindac, and etoposide.

Administration of compounds of the invention, or pharmaceutically acceptable salts, solvates, stereoisomers, or prodrugs thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for compounds of this invention is oral. Preferred routes of administration for the second active agents or ingredients of the invention are known to those of ordinary skill in the art. See, e.g., Physicians' Desk Reference, 1755–1760 (56$^{th}$ ed., 2002).

In one embodiment of the invention, the second active agent is administered once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds of the invention and any optional additional active agents concurrently administered to the patient.

5. EXAMPLES 5.1 Purification and Identification of Synthesized Compounds

High Performance Liquid Chromatography (HPLC) was employed to purify and identify the representative compounds of this invention following their syntheses. Following conditions were used: Agilent LCMS-Method: Qc1.m; Column: Polaris C18 5μ 4.6×30 mm; Gradient: 0–100% solvent B in 2 min.; Run time: 2.5min; Solvent A: methanol/water/TFA=10/90/0.1 by volume; Solvent B: methanol/water/TFA=90/10/0.1 by volume; Detection: 220 nm, 254 nm and ELSD (Evaporative light scattering).

5.2 2-Methyl-5-ethoxy-carbonyl-4-hydroxy-thiazole

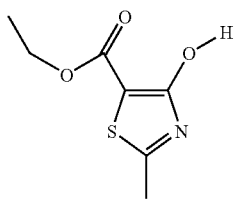

Diethyl-2-bromo malonate (168 g, 0.7 mol) was added to thioacetamide (52.5 g, 0.7 mol) in 400 ml of toluene. The mixture was refluxed for 1 hour. The reaction mixture was then cooled down to room temperature, and then was filtered through a pad of celite. Toluene was then removed in vacuo to give a viscous oil as crude product, which was stirred with 500 ml water until solid precipitated out. The solid was filtered off and washed with water (3×300 ml) and then with petroleum ether, and dried under high vacuum to give 55 g of the title compound (yield: 42%; LC: Retention Time=1.24 min; MS: M+1=188).

5.3 2-Bromomethyl-5-ethoxy-carbonyl-4-hydroxy-thiazole

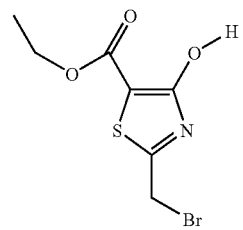

2-Methyl-5-ethoxy-carbonyl-4-hydroxy-thiazole (45 g, 0.24 mol) was dissolved in 1 L of carbon tetrachloride. The solution was cooled down to 0° C. N-Bromo succinimide (43 g, 0.24 mol) was added portion-wise at 0° C. The reaction mixture was stirred at 0° C. for 1 hour and then warmed to room temperature. The reaction mixture was stirred at room temperature for overnight. The reaction mixture was then passed through a short pad of celite. Removal of solvent gave crude product as solid, which was washed with ethyl acetate/hexane (1/3) three times (1×40 ml; 2×20 ml) to give 30 g of the title compound (yield: 50%; LC: Retention Time=1.66 min; MS: M+1=267).

5.4 2-Bromomethyl-5-ethoxy-carbonyl-4-tosyl-thiazole

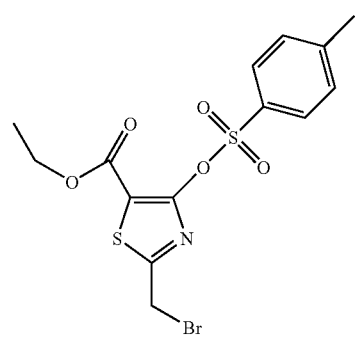

2-Bromomethyl-5-ethoxy-carbonyl-4-hydroxy-thiazole (8 g, 0.03 mol) was dissolved in 80 ml of chloroform. The solution was then cooled down to 0° C. p-Toluenesulfonyl chloride (5.7 g, 0.03 mol) was added, followed by slow addition of triethylamine (3.64 g, 0.036 mol) at 0° C. The reaction was monitored by TLC and LCMS. After the reaction was done, solvent was evaporated and the crude product was then purified by column chromatography to give 8.5 g of title product (yield 67%; LC: Retention Time=2.05 min; MS: M+1=421).

5.5 2-Piperidin-1-ylmethyl-4-(toluene-4-sulfonyloxy)-thiazole-5-carboxylic acid ethyl ester

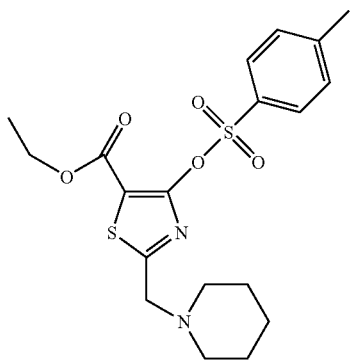

In a 500 mL round bottom flask, 2-bromomethyl-5-ethoxy-carbonyl-4-tosyl-thiazole (51.3 g, 0.122 mol) was dissolved in 300 mL of THF. Then, piperidine (31.29 g, 0.366 mol) was added slowly over 10 minutes. The mixture was stirred at room temperature over 3 hours until the completion of reaction, which was monitored by TLC and LCMS. Excess piperidine and THF were removed in vacuo followed by addition of 10 mL of water. The aqueous layer was then extracted with ethyl acetate three times (50 mL×3). The combined ethyl acetate layer was concentrated to give 35.8 g of the title compound (yield: 69%; LC: Retention time=1.65 min; MS: M+1=425). The product was used in next step without further purification.

The following compounds were prepared using the procedure described in Example 5.5.

| Structure | LC Retention time (minutes) | MS |
|---|---|---|
| | 1.717 | M + 1 = 439 |
| 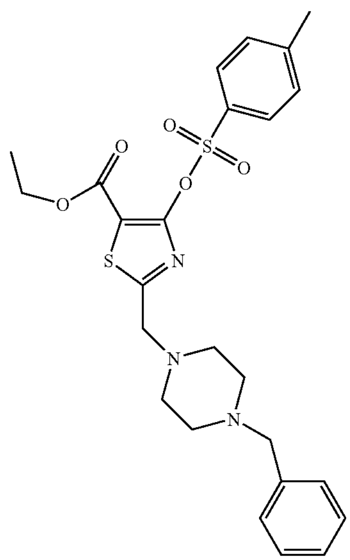 | 1.807 | M + 1 = 516 |
| 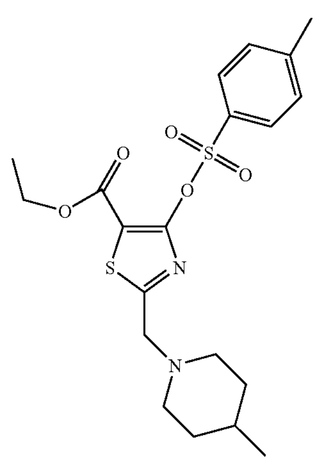 | 1.733 | M + 1 = 439 |

-continued

| Structure | LC Retention time (minutes) | MS |
|---|---|---|
| 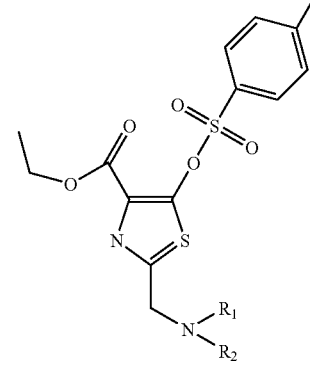 | 1.703 | M + 1 = 439 |

5.6  2-Piperidin-1-yl-methyl-4-propylamino-thiazole-5-carboxylic acid ethylester

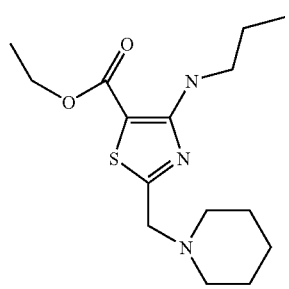

2-Piperidin-1-yl-methyl-4-(toluene-4-sulfonyloxy)-thiazole-5-carboxylic acid ethylester (5.6 g, 12.7 mmol) was dissolved in 40 mL of 1,4-dioxane in a sealed tube. 1-Propylamine (3.7 g, 63.5 mmol) was then added to the reaction mixture. The reaction mixture was heated at 110° C. over 12 hours. After the reaction was completed, excess 1-propylamine and 1,4-dioxane were evaporated in vacuo to give a residue. Water (10 mL) was added and the mixture was extracted with ethyl acetate three times (3×30 mL). The combined ethyl acetate layer was dried over sodium sulfate. Removal of solvent gave crude product, which was purified by silica gel column chromatography using hexanes/ethyl acetate (10/1) to give 2.2 g of the title compound (yield: 55%; LC: Retention time: 1.626 min; MS: M+1=312).

The following compounds were prepared using the procedure described in Example 5.6.

| Structure | LC Retention time (min) | MS |
|---|---|---|
| 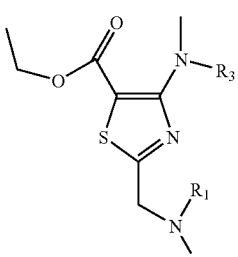 | 1.659 | M + 1 = 326 |
| 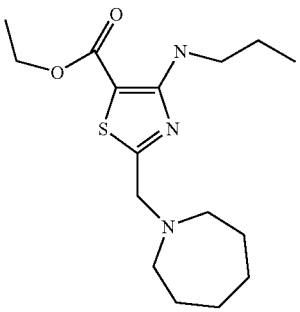 | 1.511 | M + 1 = 356 |
| 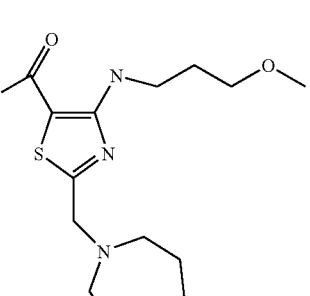 | 1.507 | M + 1 = 312 |

-continued

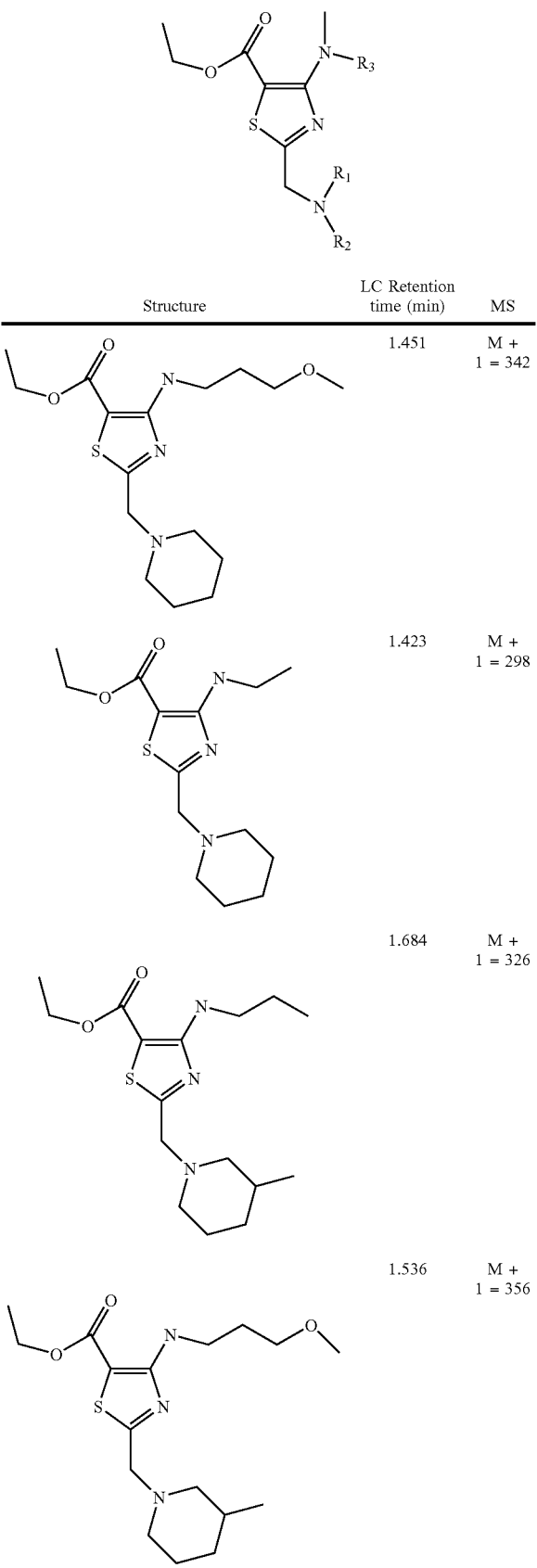

| Structure | LC Retention time (min) | MS |
|---|---|---|
| (structure) | 1.451 | M + 1 = 342 |
| (structure) | 1.423 | M + 1 = 298 |
| (structure) | 1.684 | M + 1 = 326 |
| (structure) | 1.536 | M + 1 = 356 |

-continued

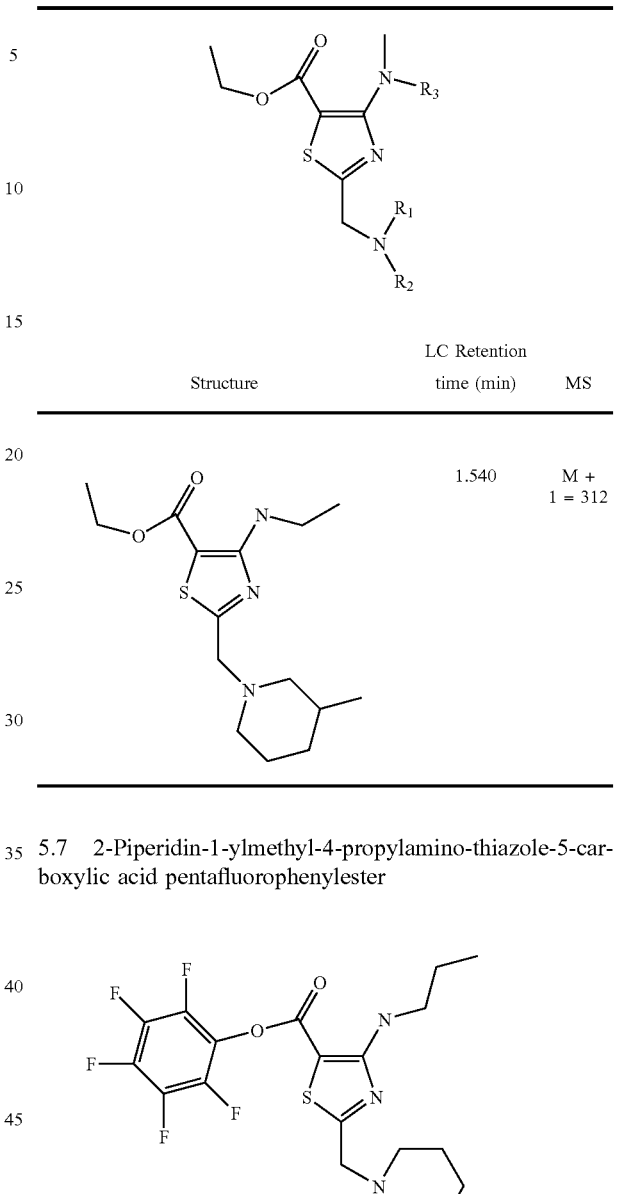

| Structure | LC Retention time (min) | MS |
|---|---|---|
| (structure) | 1.540 | M + 1 = 312 |

5.7 2-Piperidin-1-ylmethyl-4-propylamino-thiazole-5-carboxylic acid pentafluorophenylester 5 2-Piperidin-1-yl-methyl-4-propylamino-thiazole-5-carboxylic acid ethyl ester (0.253 g, 0.813 mmol) was dissolved in 8 ml of ethanol. 1N sodium hydroxide (3.25 ml) was then added, and the resulting mixture was heated at 60° C. for 1 hour. After the reaction was completed, solvent was evaporated to give a crude product. The crude product was mixed with o-benzotriazol-1-yl-N,N,N'N'-tetramethyluronium hexafluorophosphate (HBTU) (0.462 g, 1.22 mmol) and pentafluorophenol (0.299 g, 1.626 mmol) in 10 ml of THF at 50° C. for 2 hours. Removal of solvent gave crude product, which was purified by silica gel column using ISCO CombiFlash to give 0.233 g of the title compound (yield: 64%).

The following compounds were prepared using the procedure described in Example 5.7.

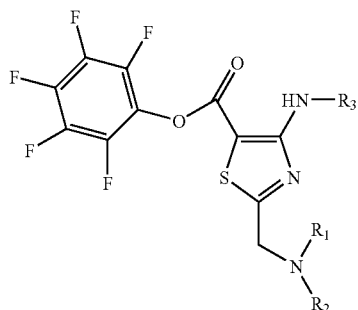
| Structure | LC Retention time (min) | LC/MS |
|---|---|---|
| 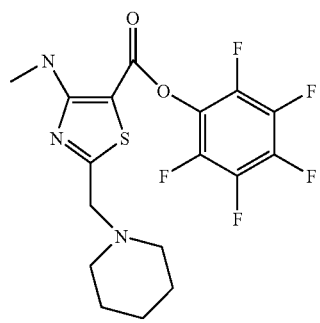 | 1.334 | M + 1 = 422 |
| 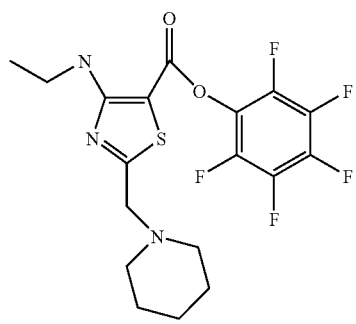 | 1.415 | M + 1 = 436 |
| 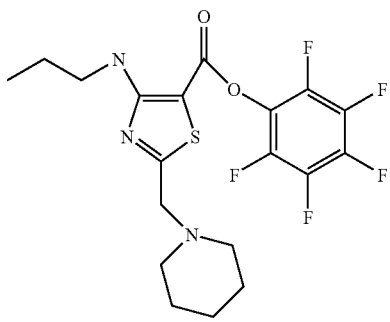 | 1.478 | M + 1 = 450 |

-continued
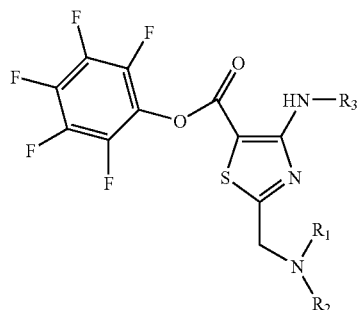
| Structure | LC Retention time (min) | LC/MS |
|---|---|---|
| 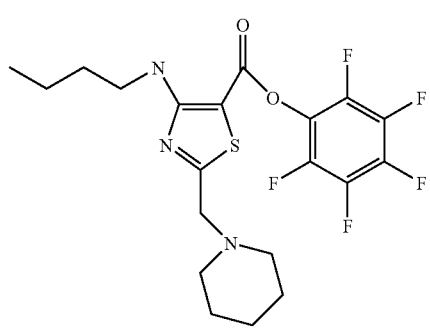 | 1.560 | M + 1 = 464 |
| 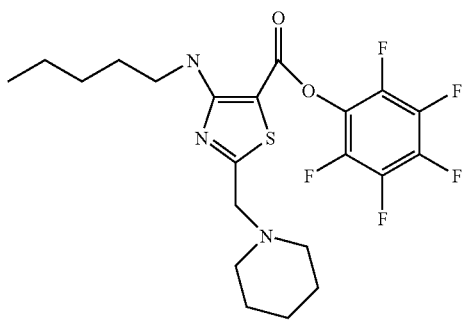 | 1.626 | M + 1 = 478 |
| 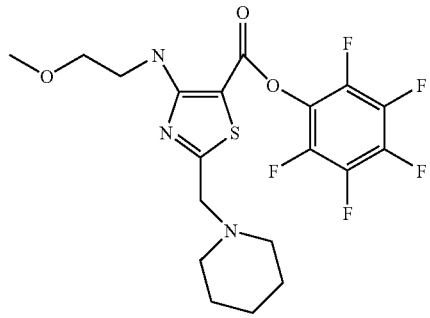 | 1.344 | M + 1 = 465 |

-continued
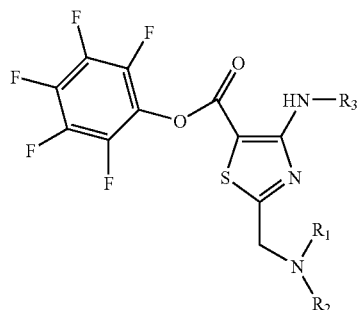
| Structure | LC Retention time (min) | LC/MS |
|---|---|---|
| 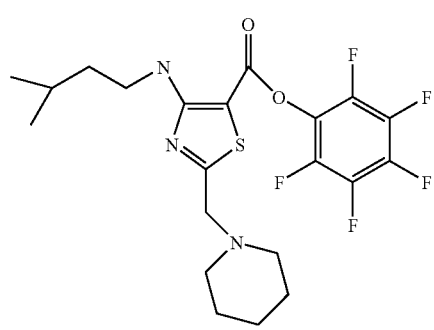 | 1.629 | M + 1 = 478 |
| 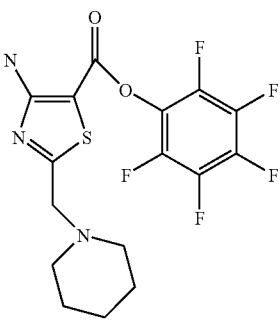 | 1.776 | M + 1 = 506 |
| 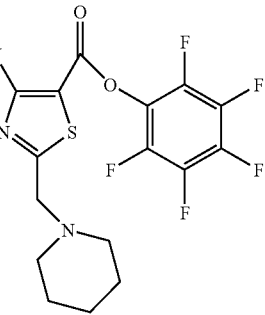 | 1.406 | M + 1 = 480 |

-continued
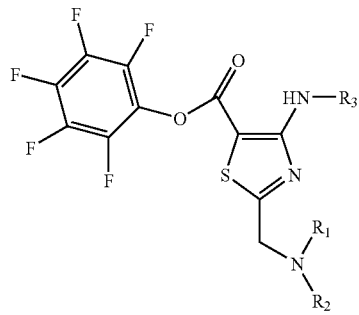
| Structure | LC Retention time (min) | LC/MS |
|---|---|---|
| 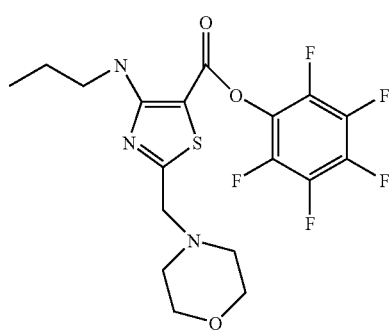 | 1.414 | M + 1 = 452 |
| 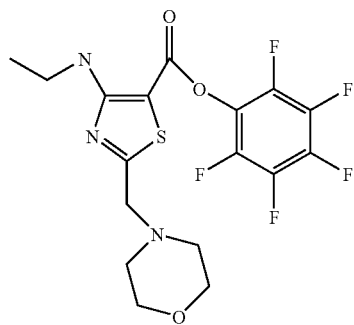 | 1.355 | M + 1 = 438 |
| 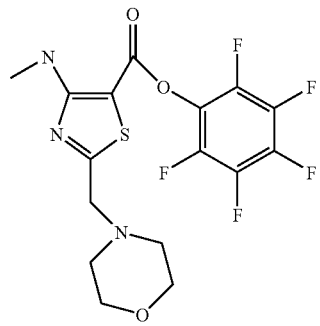 | 1.145 | M + 1 = 424 |

-continued
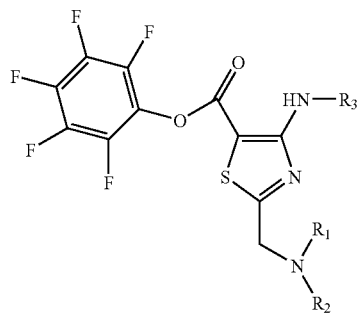
| Structure | LC Retention time (min) | LC/MS |
|---|---|---|
| 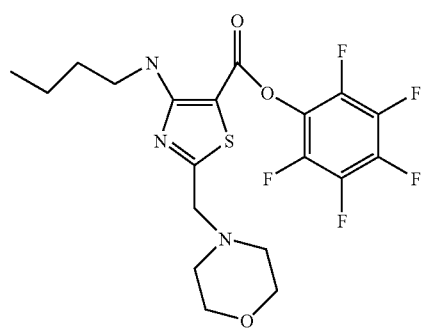 | 1.523 | M + 1 = 466 |
| 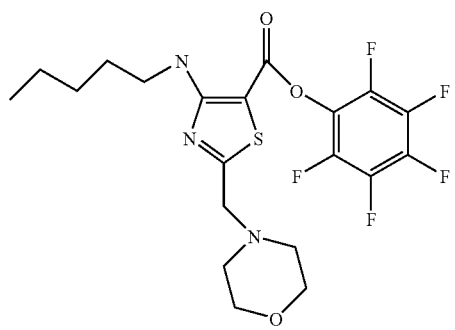 | 1.586 | M + 1 = 480 |
| 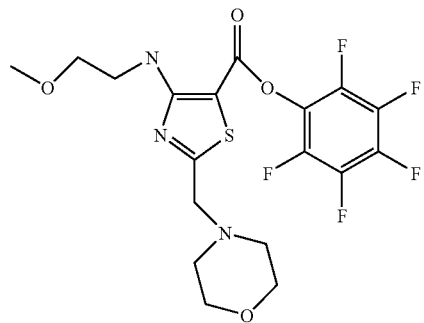 | 1.310 | M + 1 = 468 |

-continued
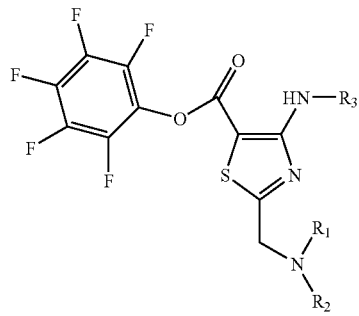
| Structure | LC Retention time (min) | LC/MS |
|---|---|---|
| 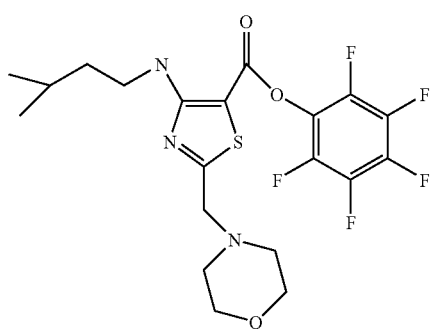 | 1.617 | M + 1 = 480 |
| 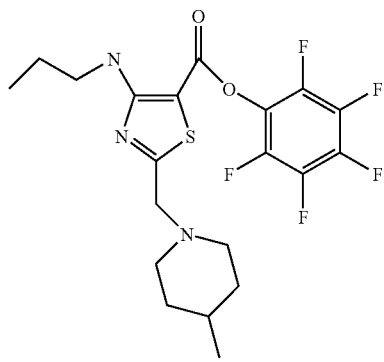 | 1.536 | M + 1 = 464 |
| 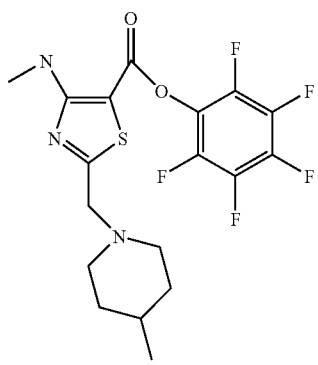 | 1.442 | M + 1 = 450 |

-continued
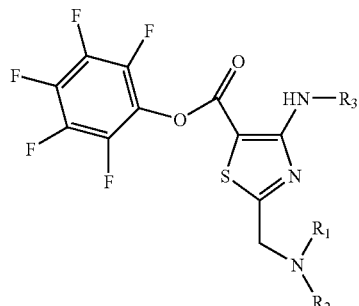
| Structure | LC Retention time (min) | LC/MS |
|---|---|---|
| 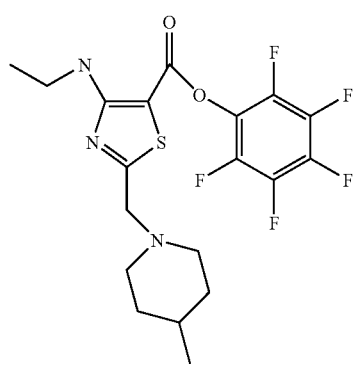 | 1.371 | M + 1 = 436 |
| 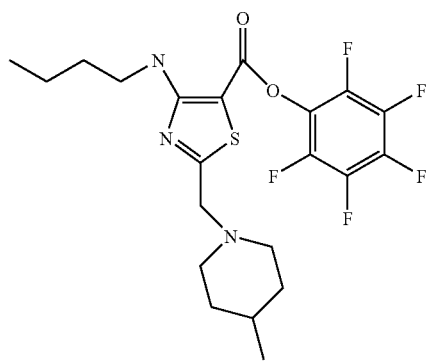 | 1.577 | M + 1 = 478 |
| 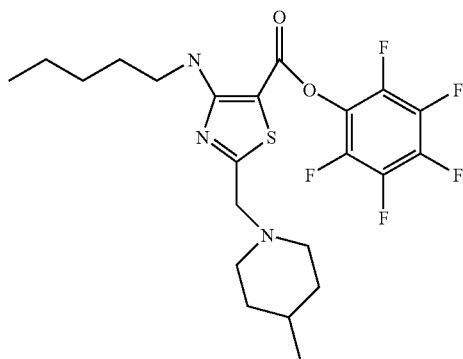 | 1.697 | M + 1 = 492 |

-continued
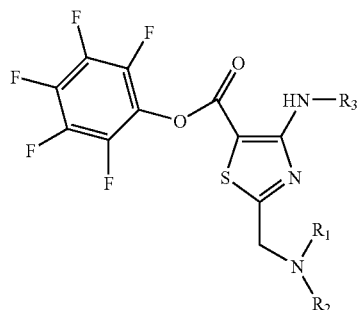
| Structure | LC Retention time (min) | LC/MS |
|---|---|---|
| 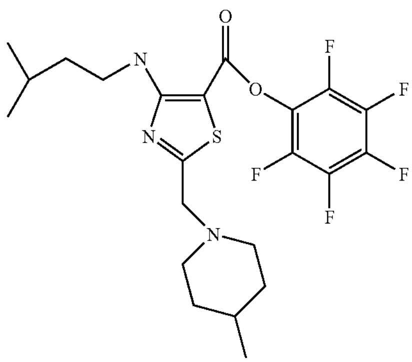 | 1.639 | M + 1 = 492 |
| 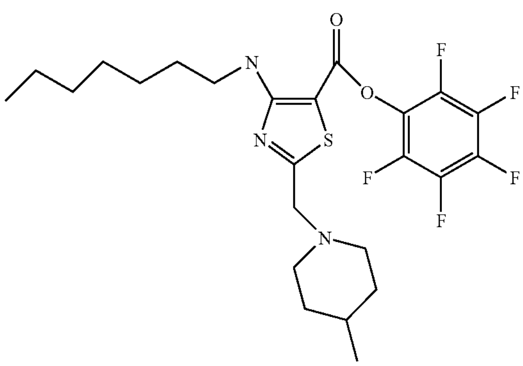 | 1.773 | M + 1 = 520 |
| 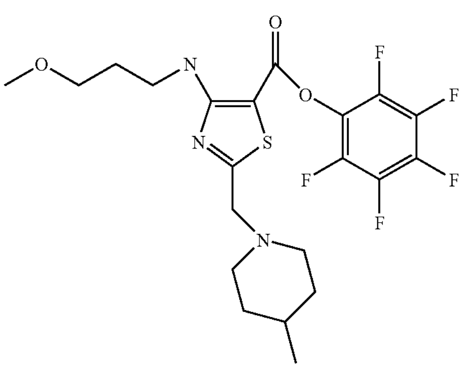 | 1.462 | M + 1 = 494 |

-continued
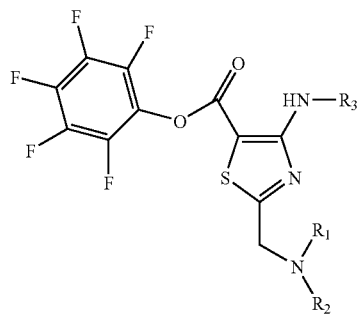
| Structure | LC Retention time (min) | LC/MS |
|---|---|---|
| 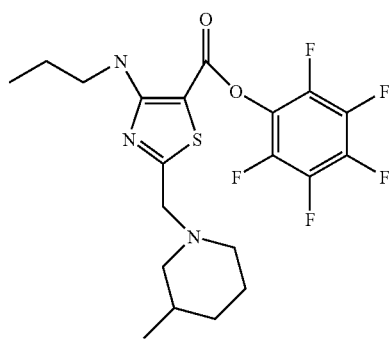 | 1.453 | M + 1 = 464 |
| 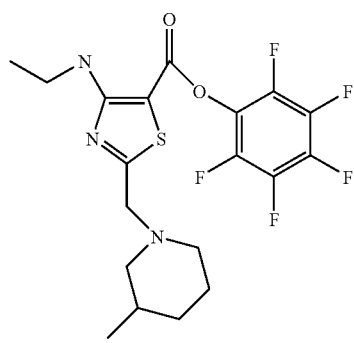 | 1.465 | M + 1 = 450 |
| 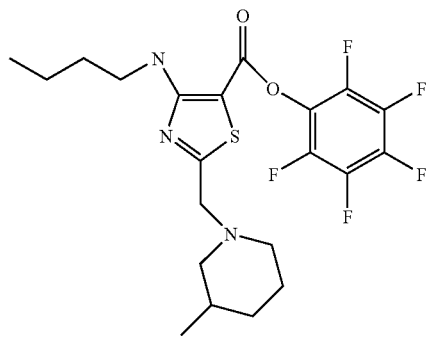 | 1.606 | M + 1 = 478 |

-continued
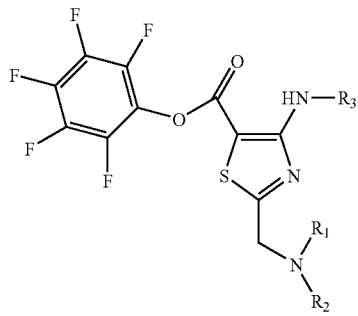
| Structure | LC Retention time (min) | LC/MS |
|---|---|---|
| 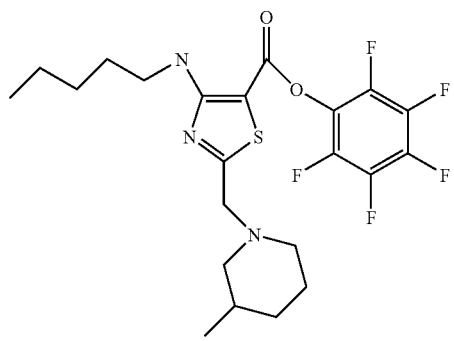 | 1.646 | M + 1 = 492 |
| 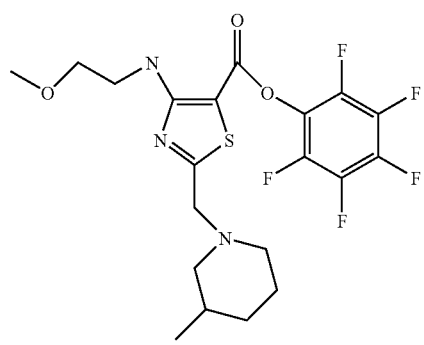 | 1.410 | M + 1 = 480 |
| 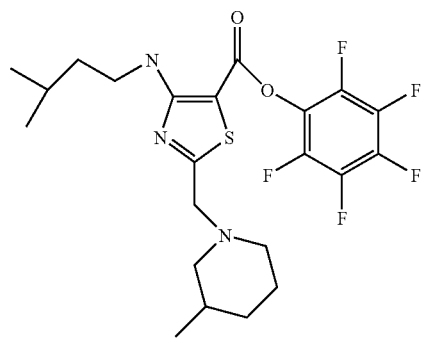 | 1.649 | M + 1 = 492 |

-continued
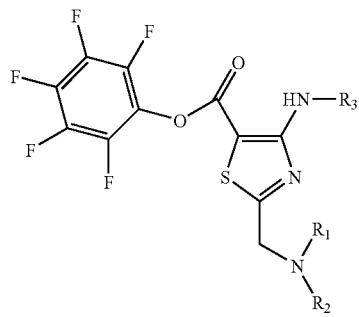
| Structure | LC Retention time (min) | LC/MS |
|---|---|---|
| 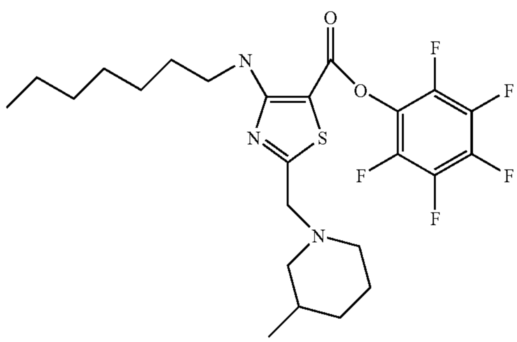 | 1.810 | M + 1 = 520 |
| 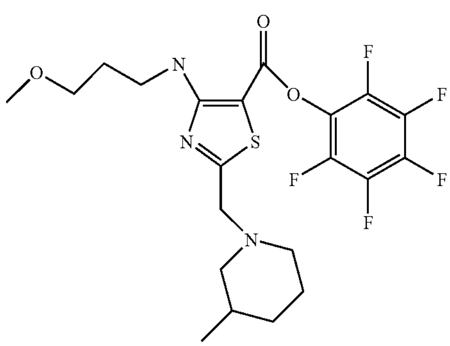 | 1.443 | M + 1 = 494 |
| 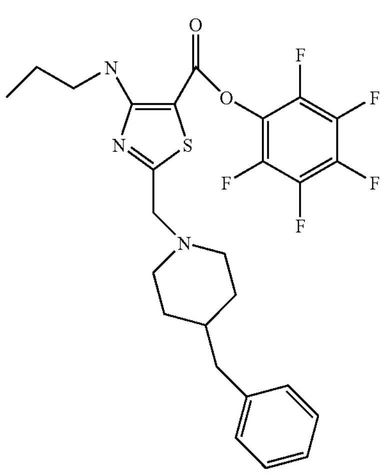 | 1.680 | M + 1 = 540 |

-continued
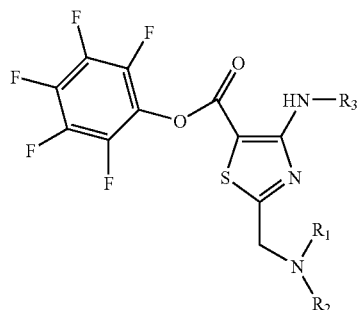
| Structure | LC Retention time (min) | LC/MS |
|---|---|---|
| 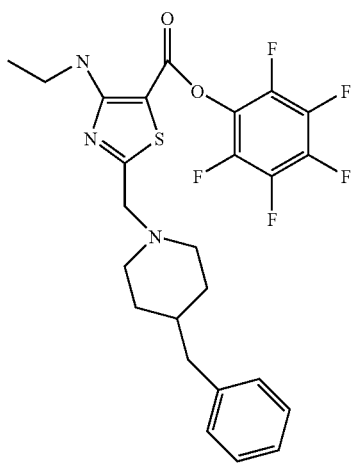 | 1.588 | M + 1 = 526 |
| 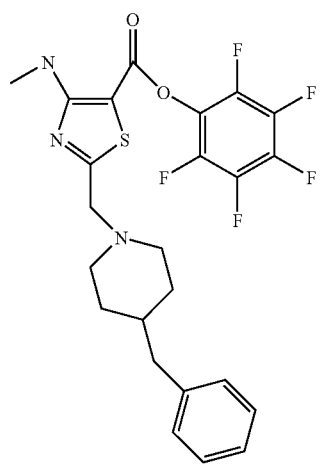 | 1.588 | M + 1 = 526 |

-continued
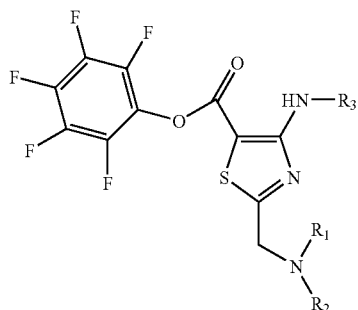
| Structure | LC Retention time (min) | LC/MS |
|---|---|---|
| 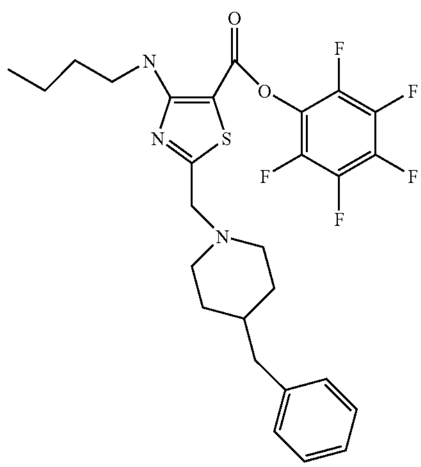 | 1.709 | M + 1 = 554 |
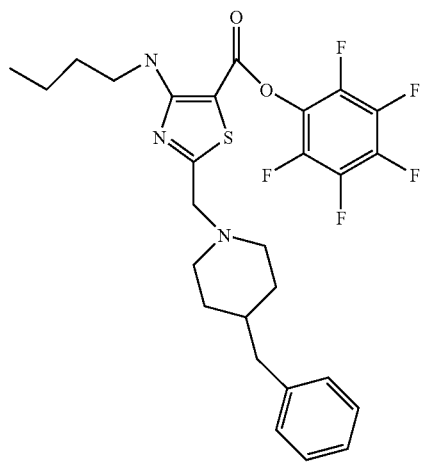
| | 1.774 | M + 1 = 568 |
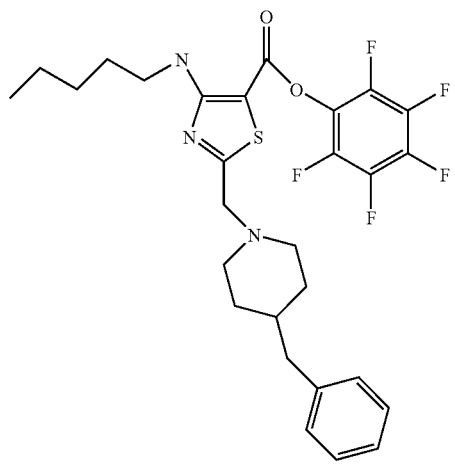

-continued
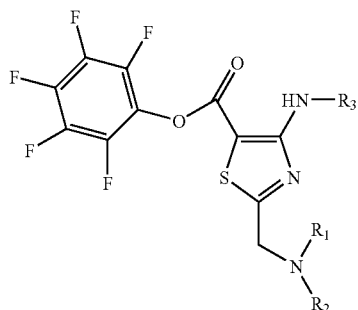
| Structure | LC Retention time (min) | LC/MS |
|---|---|---|
| 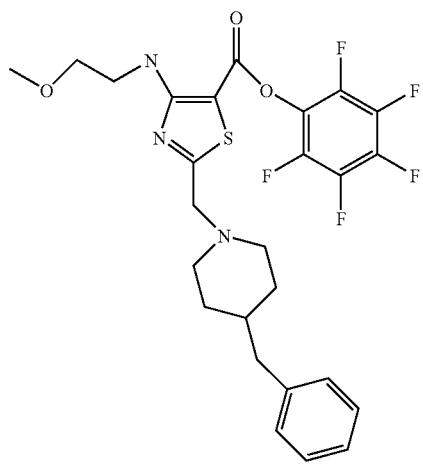 | 1.558 | M + 1 = 556 |
| 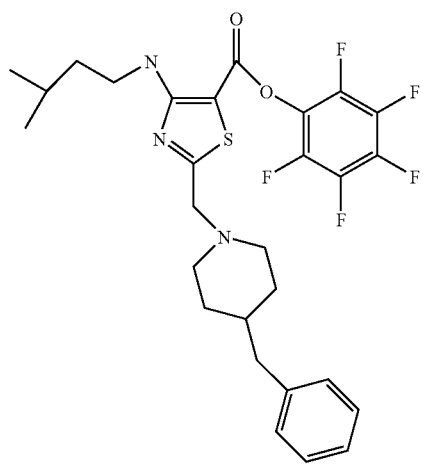 | 1.776 | M + 1 = 568 |

-continued
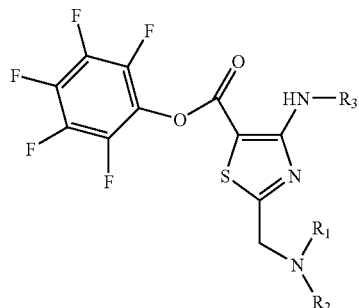
| Structure | LC Retention time (min) | LC/MS |
|---|---|---|
| 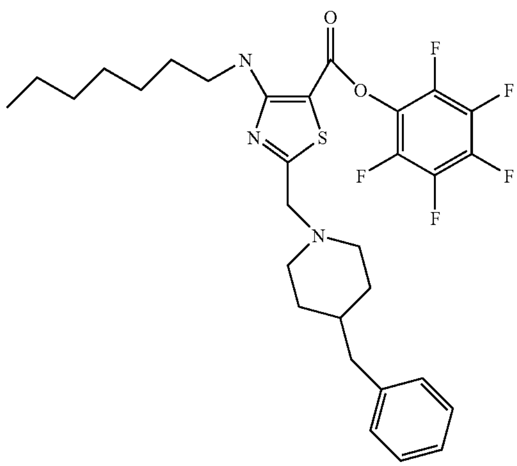 | 1.896 | M + 1 = 596 |
| 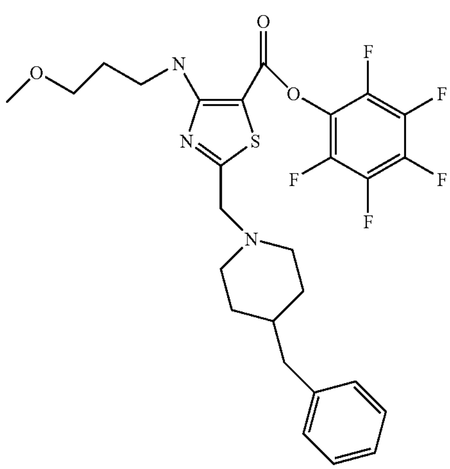 | 1.606 | M + 1 = 570 |
| 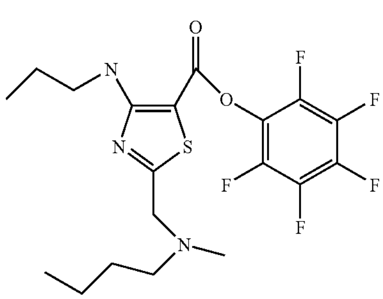 | 1.521 | M + 1 = 452 |

-continued
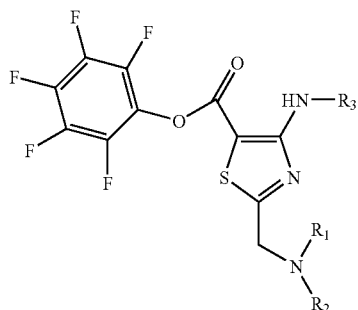
| Structure | LC Retention time (min) | LC/MS |
|---|---|---|
| 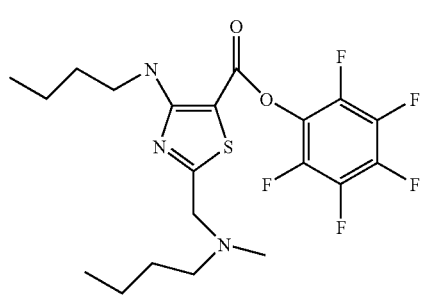 | 1.607 | M + 1 = 466 |
| 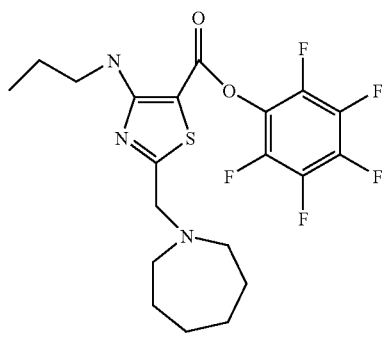 | 1.514 | M + 1 = 464 |
| 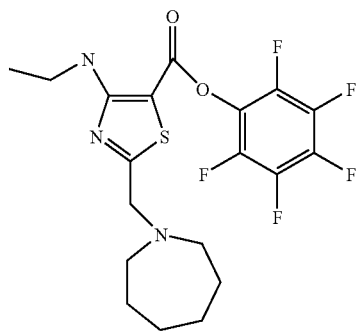 | 1.473 | M + 1 = 450 |

-continued
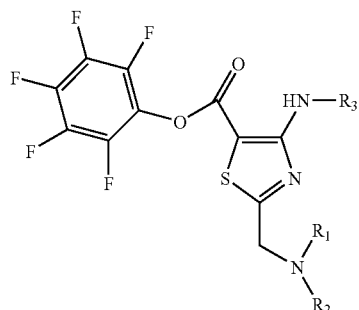
| Structure | LC Retention time (min) | LC/MS |
|---|---|---|
| 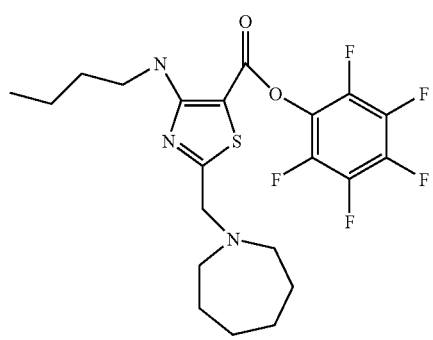 | 1.584 | M + 1 = 478 |
| 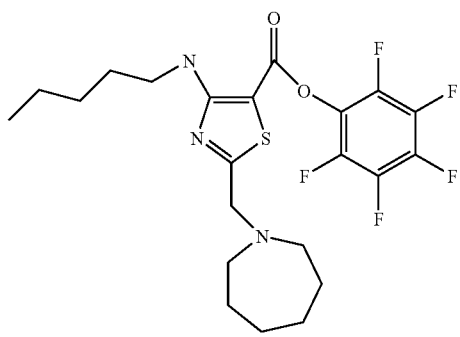 | 1.645 | M + 1 = 492 |
| 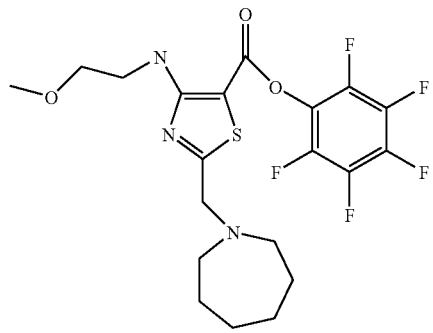 | 1.395 | M + 1 = 480 |

-continued
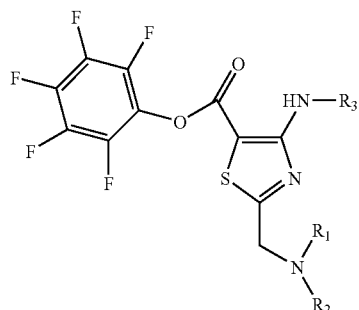
| Structure | LC Retention time (min) | LC/MS |
|---|---|---|
| 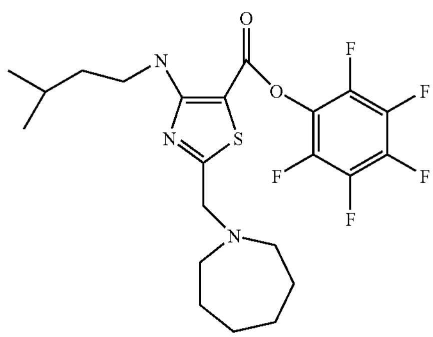 | 1.627 | M + 1 = 492 |
| 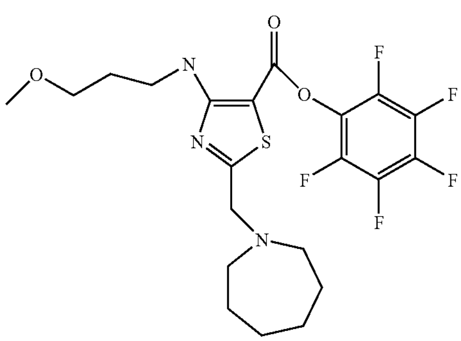 | 1.438 | M + 1 = 494 |
| 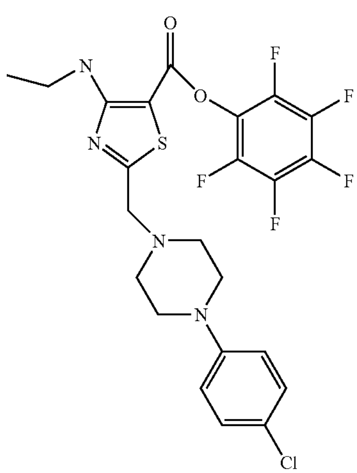 | 1.677 | M + 1 = 547 |

-continued
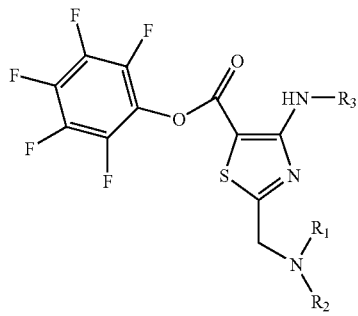
| Structure | LC Retention time (min) | LC/MS |
|---|---|---|
| 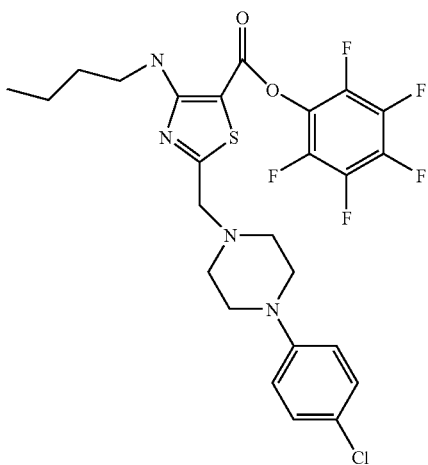 | 1.830 | M + 1 = 575 |
| 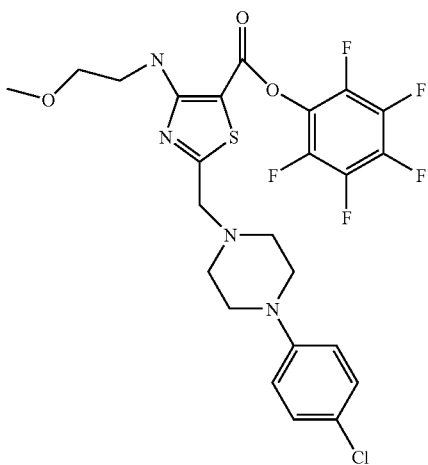 | 1.617 | M + 1 = 577 |

-continued
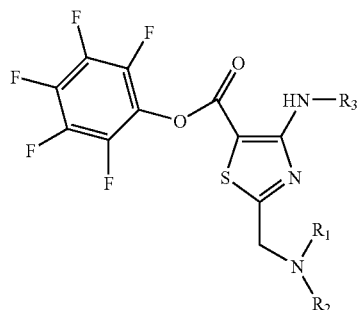
| Structure | LC Retention time (min) | LC/MS |
|---|---|---|
| 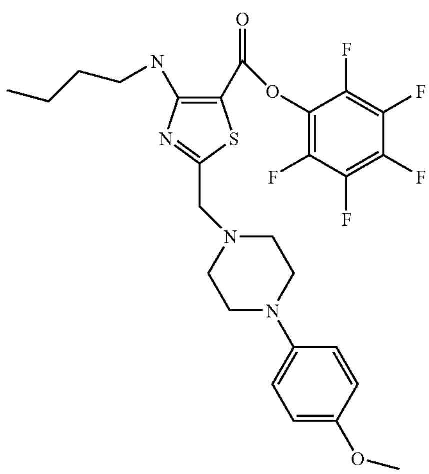 | 1.676 | M + 1 = 571 |
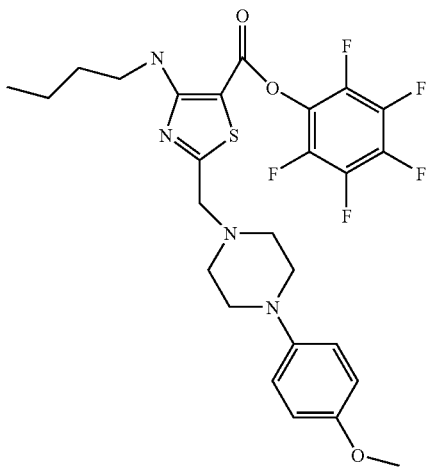
| | 1.745 | M + 1 = 585 |
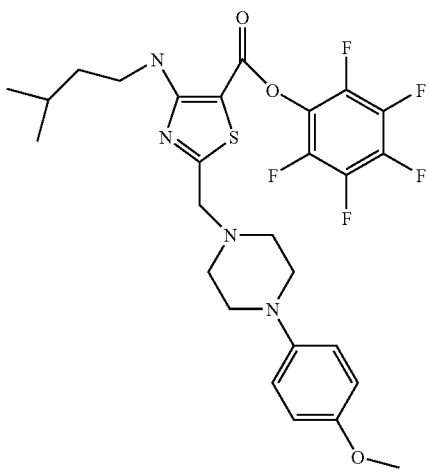

-continued
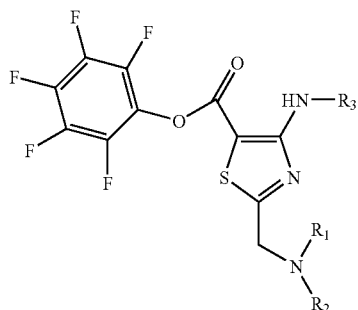
| Structure | LC Retention time (min) | LC/MS |
|---|---|---|
| 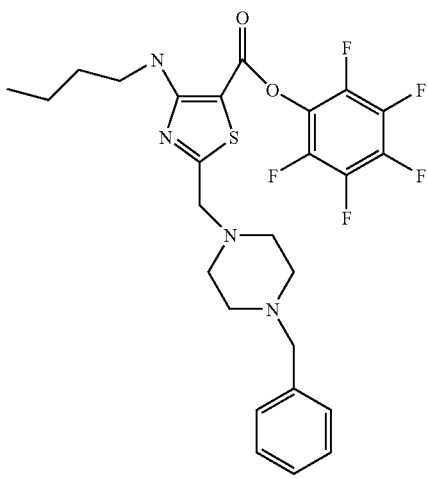 | 1.669 | M + 1 = 555 |
| 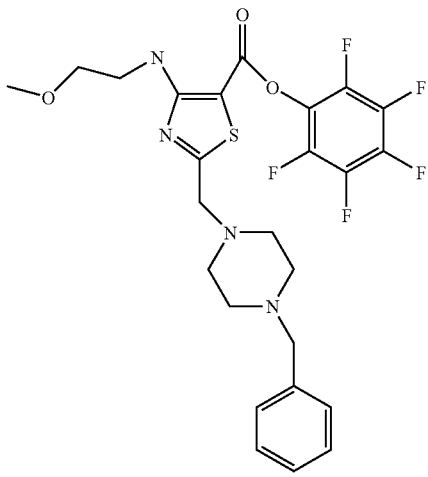 | 1.500 | M + 1 = 557 |

-continued

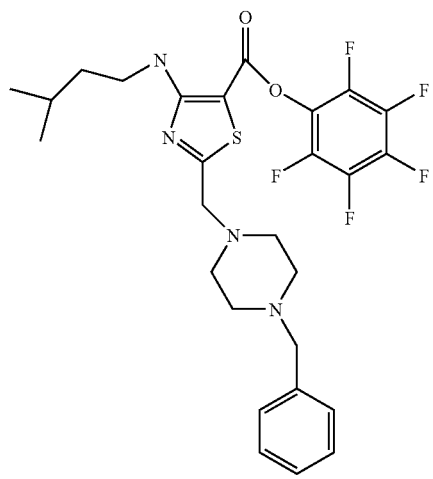

| Structure | LC Retention time (min) | LC/MS |
|---|---|---|
|  | 1.747 | M + 1 = 569 |

5.8  2-Piperidin-1-ylmethyl-4-propylamino-thiazole-5-carboxylic acid isobutyl-amide

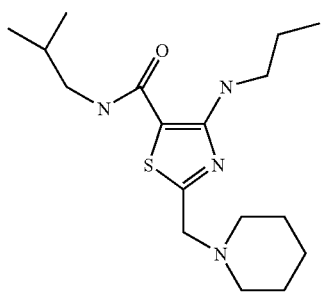

In a 40 mL vial, 2-Piperidin-1-ylmethyl-4-propylamino-thiazole-5-carboxylic acid pentafluorophenylester (217 mg, 0.469 mmol) was dissolved in 10 mL of THF. Isobutylamine (44 mg, 0.609 mmol) and polymer supported diisopropylethylamine (583 mg, 0.938 mmol) were added. The vial was sealed and heated at 60° C. over 8 hours. After the completion of reaction, the resin was filtered off and washed with THF (2×10 mL). Polymer supported Trisamine (1 g, loading: 4.1 mmoles/g) was introduced into the combined solution, and the mixture was shaken at room temperature for overnight. The resin was then filtered off and washed with THF. The combined THF was evaporated to give desired product (114 mg; yield: 69%).

The following compounds were prepared from appropriate pentafluorophenyl ester using the procedure described in Example 5.8.

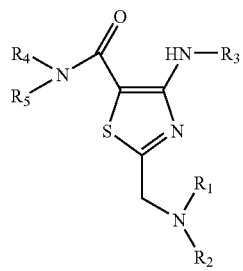
| Structure | LC Retention Time (min) | MS |
|---|---|---|
| 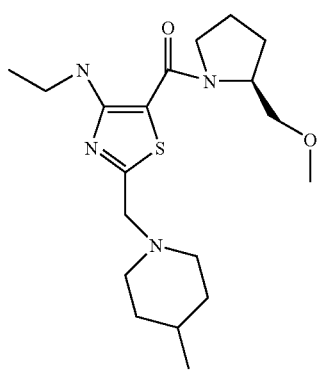 | 1.518 | M + 1 = 381 |
| 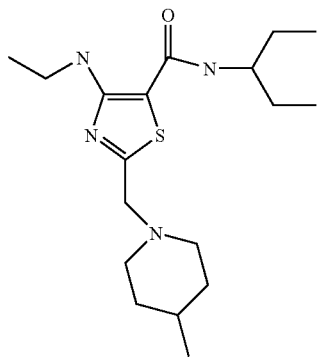 | 1.686 | M + 1 = 353 |
| 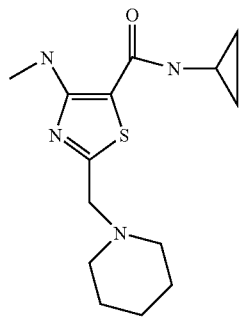 | 1.032 | M + 1 = 295 |

-continued
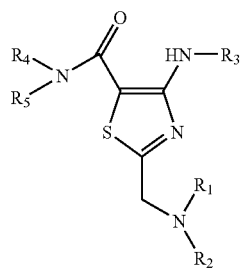
| Structure | LC Retention Time (min) | MS |
|---|---|---|
| 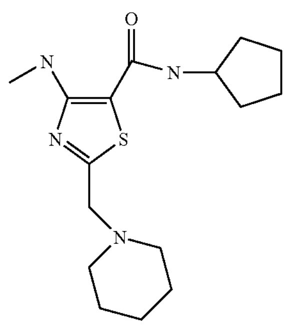 | 1.390 | M + 1 = 323 |
| 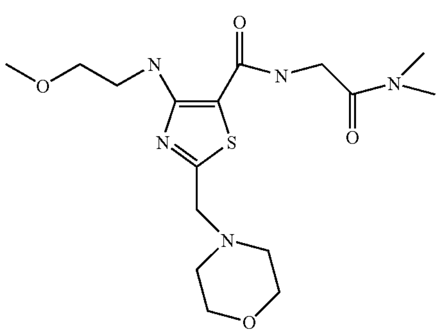 | 0.897 | M + 1 = 386 |
| 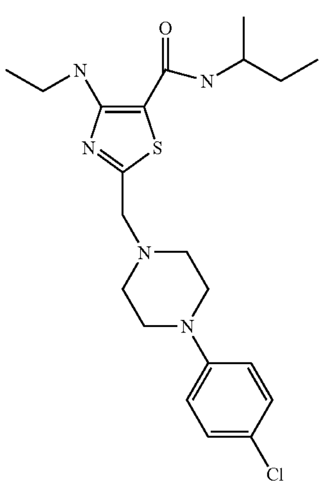 | 1.912 | M + 1 = 436 |

-continued
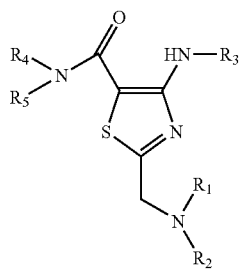
| Structure | LC Retention Time (min) | MS |
|---|---|---|
| 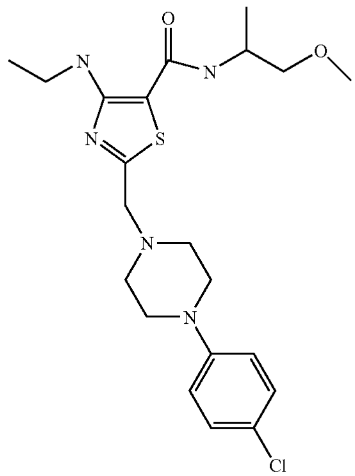 | 2.056 | M + 1 = 452 |
| 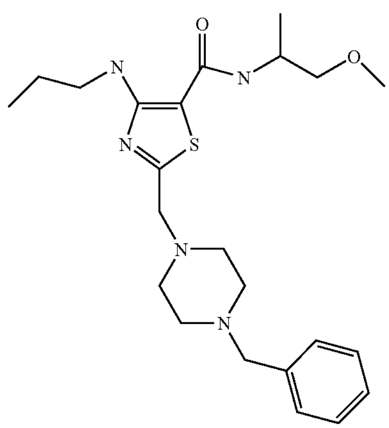 | 1.898 | M + 1 = 446 |
| 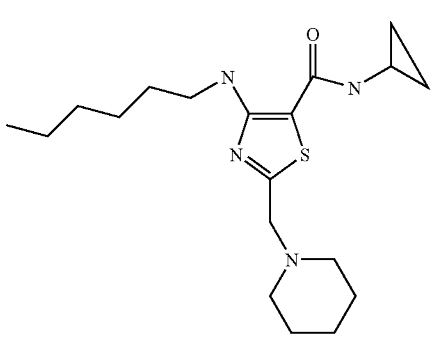 | 1.805 | M + 1 = 365 |

-continued

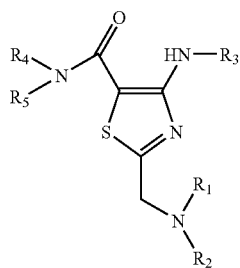

| Structure | LC Retention Time (min) | MS |
|---|---|---|
| 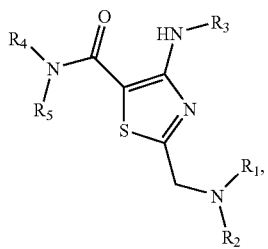 | 2.037 | M + 1 = 395 |

All of the patents, patent applications and publications referred to in this application are incorporated herein in their entireties. However, citation or identification of any reference in this application is not an admission that such reference is available as prior art to this invention. The full scope of the invention is better understood with reference to the appended claims.

The invention claimed is:

1. A compound of formula (1):

(1)

or a pharmaceutically acceptable salt, stereoisomer or solvate thereof, wherein:

$R_1$, $R_2$, $R_3$, $R_4$ and $R_5$ are each independently H, optionally substituted alkyl, optionally substituted alkenyl, optionally substituted alkynyl, optionally substituted aryl, optionally substituted heteroaryl, optionally substituted heterocycloalkyl, optionally substituted heterocycle; optionally substituted arylalkyl, optionally substituted heterocycloalkylalkyl, or optionally substituted heteroarylalkyl; or $R_1$ and $R_2$, and $R_4$ and $R_5$, with the nitrogen atom to which they are attached, independently form an optionally substituted heterocycle.

2. The compound of claim 1, wherein $R_3$ is alkyl.

3. The compound of claim 1, wherein $R_1$ and $R_2$, with the nitrogen atom to which they are attached form an optionally substituted heterocycle.

4. The compound of claim 3, wherein the heterocycle formed by $R_1$ and $R_2$ is optionally substituted piperidine.

5. The compound of claim 3, wherein the heterocycle formed by $R_1$ and $R_2$ is optionally substituted morpholine.

6. The compound of claim 3, wherein the heterocycle formed by $R_1$ and $R_2$ is optionally substituted piperazine.

7. The compound of claim 1, wherein $R_4$ is H and $R_5$ is alkyl or cycloalkyl.

8. The compound of claim 1, wherein $R_4$ is H and $R_5$ is optionally substituted aminocarbonyl.

9. The compound of claim 1, wherein $R_4$ and $R_5$, with the nitrogen to which they are attached, form an optionally substituted heterocycle.

10. The compound of claim 9, wherein the heterocycle formed by $R_4$ and $R_5$ is optionally substituted pyrrolidine.

11. The compound of claim 1, which is stereomerically pure.

12. The compound of claim 1, which is:
(S)-(4-(ethylamino)-2-((4-methylpiperidin-1-yl)methyl) thiazol-5-yl)(2-(methoxymethyl)pyrrolidin-1-yl) methanone;
4-(ethylamino)-2-((4-methylpiperidin-1-yl)methyl)-N-(pentan-3-yl)thiazole-5-carboxamide;
N-cyclopropyl-4-(methylamino)-2-(piperidin-1-ylmethyl)thiazole-5-carboxamide;
N-cyclopentyl-4-(methylamino)-2-(piperidin-1-ylmethyl) thiazole-5-carboxamide;
N-(2-(dimethylamino)-2-oxoethyl)-4-(2-methoxyethylamino)-2-(morpholinomethyl)thiazole-5-carboxamide;
N-sec-butyl-2-((4-(4-chlorophenyl)piperazin-1-yl)methyl)-4-(ethylamino)thiazole-5-carboxamide;
2-((4-(4-chlorophenyl)piperazin-1-yl)methyl)-4-(ethylamino)-N-(1-methoxypropan-2-yl)thiazole-5-carboxamide;

2-((4-benzylpiperazin-1-yl)methyl)-N-(1-methoxypropan-2-yl)-4-(propylamino)thiazole-5-carboxamide;

N-cyclopropyl-4-(hexylamino)-2-(piperidin-1-ylmethyl)thiazole-5-carboxamide; or 4-(hexylamino)-N-(pentan-3-yl)-2-(piperidin-1-ylmethyl)thiazole-5-carboxamide.

13. A pharmaceutical composition comprising a compound of formula (1):

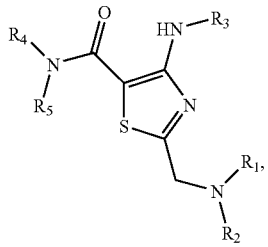

(1)

or a pharmaceutically acceptable salt, stereoisomer or solvate thereof, wherein:

$R_1$ and $R_2$, and $R_4$ and $R_5$, with the nitrogen atom to which they are attached, independently form an optionally substituted heterocycle.

14. The pharmaceutical composition of claim 13, which further comprises a pharmaceutically acceptable carrier or excipient.

15. The pharmaceutical composition of claim 14, which is a single dosage form.

16. The dosage form of claim 15, which is suitable for oral, parenteral or transdermal administration.

* * * * *